US00RE41315E

(19) United States
(12) Reissued Patent
Sonesson et al.

(10) Patent Number: US RE41,315 E
(45) Date of Reissued Patent: May 4, 2010

(54) MODULATORS OF DOPAMINE NEUROTRANSMISSION

(75) Inventors: Clas Sonesson, Billdal (SE); Bengt Andersson, Goteborg (SE); Ingela Marianne Svan, legal representative, Göteborg (SE); Susanna Waters, Goteborg (SE); Nicholas Waters, Goteborg (SE); Joakim Tedroff, Danderyd (SE)

(73) Assignee: NSAB, Filial af NeuroSearch Sweden AB, Sveringe Ballerup (DE)

(21) Appl. No.: 11/904,013

(22) PCT Filed: Dec. 22, 2000

(86) PCT No.: PCT/SE00/02675

§ 371 (c)(1),
(2), (4) Date: Jun. 18, 2002

(87) PCT Pub. No.: WO01/46146

PCT Pub. Date: Jun. 28, 2001

Related U.S. Patent Documents

Reissue of:
(64) Patent No.: 6,924,374
Issued: Aug. 2, 2005
Appl. No.: 10/168,019
Filed: Jun. 18, 2002

(30) Foreign Application Priority Data

Dec. 22, 1999 (SE) ..... 9904723

(51) Int. Cl.
*C07D 211/04* (2006.01)
*A61K 31/445* (2006.01)

(52) U.S. Cl. ..... 546/192; 514/317
(58) Field of Classification Search ..... 546/192; 514/317
See application file for complete search history.

(56) References Cited

U.S. PATENT DOCUMENTS

| | | | |
|---|---|---|---|
| 3,326,916 | A | 6/1967 | Creighton et al. |
| 3,458,521 | A | 7/1969 | Jack et al. |
| 3,539,573 | A | 11/1970 | Schmutz et al. |
| 4,202,898 | A | 5/1980 | Depoortere |
| 4,203,986 | A | 5/1980 | Joullie et al. |
| 4,267,328 | A | 5/1981 | Najer et al. |
| 4,333,942 | A | 6/1982 | Eistetter et al. |
| 4,415,736 | A | 11/1983 | Ciganek et al. |
| 4,504,660 | A | 3/1985 | Klaubert et al. |
| 4,892,875 | A | 1/1990 | Meguro et al. |
| 4,892,975 | A | 1/1990 | Neenan et al. |
| 5,026,716 | A | 6/1991 | Bianchetti et al. |
| 5,462,947 | A | 10/1995 | Svensson et al. |
| 5,502,050 | A | 3/1996 | Gross |
| 6,175,015 | B1 | 1/2001 | Yuan et al. |
| 6,903,120 | B2 | 6/2005 | Sonesson et al. |
| 6,906,120 | B1 | 6/2005 | Davis et al. |
| 6,924,374 | B2 | 8/2005 | Sonesson et al. |
| 7,417,043 | B2 | 8/2008 | Sonesson et al. |
| 2007/0149542 | A1 | 6/2007 | Sonesson et al. |
| 2007/0179185 | A1 | 8/2007 | Sonesson et al. |

FOREIGN PATENT DOCUMENTS

| | | |
|---|---|---|
| CN | 1117966 | 3/1996 |
| CN | 1230180 | 9/1999 |
| EP | 0 060 179 | 9/1982 |
| EP | 0 094 159 | 11/1983 |
| EP | 0 369 887 | 5/1990 |
| EP | 0 533 266 | 3/1993 |
| EP | 0 533 267 | 3/1993 |

(Continued)

OTHER PUBLICATIONS

Hansch et al., "A Survey of Hammett Substituent Constants and Resonance and Field Parameters", Chem. Rev., vol. 91, pp. 165–195, 1991.
Bradbury et al., "Biochemical Changes Caused by the Infusion Into the Substantia Nigra of the Rat of MPTP and Related Compounds Which Antagonise Dihydropteridine Reductase", Neuropharmacology, vol. 25, No. 6, pp. 583–586, 1986.
Nacci et al., "Richerche Su Sostanze Ad Attivita Antiblastica", Farmaco—Ed. Sc., vol. 28, Fasc. 5, pp. 399–410, 2007.

(Continued)

*Primary Examiner*—Rita J Desai
(74) *Attorney, Agent, or Firm*—Buchanan Ingersoll & Rooney PC

(57) ABSTRACT

New 3-substituted 4-(phenyl-N-alkyl)-piperazine and 4-(phenyl-N-alkyl)-piperidine compounds of Formula (1) wherein X is N, CH, or C, however X may only be C when the compound comprises a double bind at the dotted line; $R_1$ is $CF_3$, $OSO_2CF_3$, $OSO_2CH_3$, $SOR_7$, $SO_2R_7$, $COR_7$, CN, $OR_3$, $NO_2$, $CONHR_3$, 3-thiophene, 2-thiophene, 3-furane, 2-furane, F, Cl, Br, or I; $R_2$ is F, Cl, Br, I, CN, $CF_3$, $CH_3$, $OCH_3$, OH, and $NH_2$; $R_3$ and $R_4$ are independently H or a $C_1$-$C_4$ alkyl; $R_5$ is a $C_1$-$C_4$ alkyl, an allyl, $CH_2SCH_3$, $CH_2CH_2OCH_3$, $CH_2CH_2CH_2F$, $CH_2CF_3$, 3,3,3-trifluoropropyl, 4,4,4-trifluorobutyl, or —$(CH_2)R_6$; $R_6$ is a $C_3$-$C_6$ cycloalkyl, 2-tetrahydrofurane, or 3-tetrahydrofurane; $R_7$ is a $C_1$-$C_3$ alkyl, $CF_3$, or $N(R_4)_2$, and pharmaceutically acceptable salts thereof are disclosed. Also pharmaceutical compositions comprising the above compounds and methods wherein the above compounds are used for treatment of disorders in the central nervous system are disclosed.

(1)

12 Claims, No Drawings

FOREIGN PATENT DOCUMENTS

| | | | |
|---|---|---|---|
| EP | 0 533 268 | | 3/1993 |
| EP | 0659743 | A1 | 6/1993 |
| EP | 0 675 118 | | 10/1995 |
| EP | 1 240 141 | | 11/2003 |
| EP | 1 419 773 | | 5/2004 |
| EP | 1 240 142 | | 10/2005 |
| GB | 850662 | | 10/1960 |
| GB | 1060160 | | 3/1967 |
| GB | 1 560 271 | | 2/1980 |
| GB | 2 027 703 | | 2/1980 |
| GB | 2 078 746 | | 1/1982 |
| GB | 2 083 476 | | 3/1982 |
| JP | 2000 086603 | | 3/2000 |
| NL | 6510107 | | 2/1966 |
| WO | WO 89/05799 | | 6/1989 |
| WO | WO 91/09594 | | 7/1991 |
| WO | WO 92/18475 | | 10/1992 |
| WO | WO 93/00313 | | 1/1993 |
| WO | WO 93/04684 | | 3/1993 |
| WO | WO 97/03986 | | 7/1996 |
| WO | WO 98/11068 | | 3/1998 |
| WO | WO 00/03713 | | 1/2000 |
| WO | WO 00/78728 | | 12/2000 |
| WO | WO 01/46144 | | 6/2001 |
| WO | WO 01/46145 | | 6/2001 |
| WO | WO 02/05819 | | 1/2002 |
| WO | WO 02/059108 | A1 | 8/2002 |
| WO | WO 2004/099150 | A2 | 11/2004 |
| WO | WO 2005/019215 | A1 | 3/2005 |
| WO | WO 2005/121087 | A1 | 12/2005 |
| WO | WO 2005/121088 | A1 | 12/2005 |
| WO | WO 2005/121092 | A1 | 12/2005 |
| WO | WO 2007/042295 | A1 | 4/2007 |
| WO | WO 2007/065655 | A1 | 6/2007 |

OTHER PUBLICATIONS

Grunblatt et al., "Potent Neuroprotective and Antioxidant Activity of Apomorphine in MPTP and 6–Hydroxydopamine Induced Neurotoxicity", J. Neural Transm. Suppl., vol. 55, pp. 57–70, 1999.

Grunblatt et al., "Neuroprotective Strategies in Parkinson's Disease Using the Models of 6–Hydroxydopamine and MPTP", Ann NY Acad. Sci., vol. 899, pp. 262–273, 2000.

International Search Report dated Oct. 18, 2005, issued in PCT Application No. PCT/EP2005/006147.

Journal Chem. Society, Bergel et al., 1944, pp. 261–264, Beiltsein Registry No. 183878 and 206256, Bielstein Institute for Organic Chemistry, Frankfurt–Main, Germany.

Chemical Abstract CA 132:35590, Synthesis of piperidine analogs of 1–(3–chloropheynl)piperazine, a well known serotonin ligand, Radl, et al., Journal of Heterocyclic Chemistry (1999), 36(4). 1017–1022.

Chemical Abstract CA 116:250000, Quantitative structure—metabolism relationship analyses of MAO—mediated toxication of 1–methyl–4–phenyl–1,2,3,6–tetrahydropyridine and analogs, Altomare, et al., Chemical Research in Toxicology (1992), 5(3), 366–75.

Chemical Abstract CA 129:49313, Mono—and difunctional nitrogen mustard analogs of the DNA minor groove binder pibenzimol. Synthesis, cytotoxicity and interaction with DNA, Smaill, et al., Anti–Cancer Drug Design (1998) 13(3), 221–242.

Chemical Abstract CA 128:321617, Practical application of the palladium–catalyzed amination in phenylpiperazine synthesis: an efficient synthesis of a metabolite of the antipsychotic agent aripiprazole, Morita, et al., Tetrahedron (1998), 54(19), 4811–4818.

Chemical Abstract CA 123:143666, Synthesis of 5–and 6–membered heterocycles by a strategy combining SNAr and SRN1 reactions, Beugelmans, et al., Bulletin de la Societe Chimique de France (1995), 132(3), 306–13.

Chemical Abstract CA 107:39724, Pyridonecarboxylic acids as antibacterial agents. Part 6. A new synthesis of 7H–pyrido [1,2,3–de][1,4]benzoxazine derivatives including an antibacterial agent, ofloxacin, Egawa, et al., Chemical & Pharmaceutical Bulletin (1986), 34(10), 4098–102.

Chemical Abstract CA 106:138355, Reaction of spiro[4H–3, 1–benzoxazine–4–4'–piperidin]–2(1H)–one derivatives and related compounds with phosphorus oxychloride, Takai, et al., Chemical & Pharmaceutical Bulletin (1986), 34(5), 1901–6.

Chemical Abstract CA 97:109953, Studies on antimalarials. III. Synthesis and antimalarial effects of some derivatives of 2,4–diamino–6–substituted piperazinylquinazolines, Zhang, et al., Yaoxue Xuebao (1981), 16(6), 415–24.

Chemical Abstract CA 95:237, N–(Aminophenyl)oxamic acids and esters as potent, orally active antiallergy agents, Klaubert, et al., Journal of Medicinal Chemistry (1981) 24(6), 742–8.

Chemical Abstract CA 93:94913, Cine and tele substitutions in the reaction of 2,3–dinitroaniline with secondary amines, Self, et al., Journal of the Chemical Society, Chemical Communications (1980), (6), 281–2.

Chemical Abstract CA 77:122113, Antimalarial drugs. 25. Folate antagonists. 3. 2,4–Diamino–6–(heterocyclic)quinazolines, a novel class of antimetabolites with potent antimalarial and antibacterial activity, Elslager, et al., Journal of Medicinal Chemistry (1972), 15(8), 827–36.

Chemical Abstract CA 71:29130, Comparison of Schistosomicidal activity of xanthenones and 4–methyl–3–chloroanilines and their hydroxymethyl analogs in Swiss mice and Syrian hamsters infected with Schistosma mansoni, Berberian et al., Journal of Medicinal Chemistry (1969), 12(4), 607–10.

Chemical Abstract CA 66:37889, A facile synthesis of piperazines from primary amines, Henry, Journal of Heterocyclic Chemistry (1966), 3(4), 503–11.

Bloom et al. (Editors), Psychopharmacology—The Fourth Generation of Progress, Chapter 21, pp. 227, 237; Chapter 22, pp. 245, 254; Chapter 25, pp. 283, 292; Chapter 26, pp. 295–301; Chapter 66, pp. 759–760, 1725, 744–746; Chapter 68, pp. 787, 793–795; Chapter 80, pp. 921–925, 927–028; Chapter 101, pp. 1205, 1207–1209; Chapter 111, pp. 1311, 1317, 1318, 1320; Chapter 126, pp. 1479–1482; Chapter 137, pp. 1591, 1600; Chapter 138, pp. 1609–1610, 1612 (1995) Raven Press, New York, New York, USA.

Carlsson et al., Interactions Between Glutamatergic and Monoaminergic Systems within the Basal Ganglia—Implications for Schizophrenia and Parkinson's Disease, TINS (1990), pp. 272–276, vol. 13, No. 7, Elsevier Science Publishers Ltd., United Kingdom.

Coyle, et al., Alzheimer's Disease: A Disorder of Cortical Cholinergic Innvervation, Science, vol. 219, Mar. 1983, pp. 1184–1190.

Feldman, et al., Principles of Neuropsychopharmacology, Chapter 17—Mind Altering Drugs, (1997), pp. 731, 762–763, Sinauer Associates, Inc., Publishers, Sunderland, Massachussetts, USA.

Gessner et al., Synthesis and Dihydropteridine Reductase Inhibitory Effects of Potential Metabolites of the Neurotoxin 1–Methyl–4–phenyl–1,2,3,6–tetrahydropyridine, Journal of Medicinal Chemistry, American Chemical Society, vol. 28, No. 3, 1985, pp. 311–317.

V. Nacci, et al., Antiblastic Substances. Lil. Tylophorine Analogs. 1. Synthesis and Cytostotic and Cytoxic Activity of 4–(3,4–dimethoxyphenyl)piperidine, Farmaco, Edizione Scientifica, vol. 328, No. 5, 1973, pp. 399–410.

Sonesson, et al., Substituted (S)–Phenylpiperidines and Rigid Congeners as Preferential Dopamine Autoreceptor Antagonists: Synthesis and Structure—Activity Relationships, Journal of Medicinal Chemistry (1994), 37, pp. 2735–2753.

Strange, Philip G., Antipsychotic Drugs: Importance of Dopamine Receptors for Mechanisms of Therapeutic Actions and Side Effects, Pharmacol Rev 53:119–133, (2001), vol. 53, No. 1.

Wolff, Manfred E., Burger's Medicinal Chemistry—4$^{th}$ Edition, Part III, John Wiley & Sons, 1979, pp. 872–873.

Examiner's first report dated Feb. 3, 2003, on Australian patent application No. 25705/01 corresponding to USPN 6,906,120.

Examiner's first report dated Feb. 3, 2003, on Australian patent application No. 25705/01 corresponding to USPN 6,924,374.

English translation of Jul. 12, 2006, Korean Official Action issued in counterpart Korean Application No. 2005–7024520 corresponding to U.S. Appl. No. 11/016,967.

Mar. 19, 2004, office action in Chinese application No. 00818258.2 which is counterpart to USPN 6,924,374, and instructions for response.

International Search Report and International Preliminary Examination Report dated Aug. 6, 2001, issued in PCT/SE00/02675 which is counterpart to USPN 6,924,374.

International Search Report and International Preliminary Examination Report dated Aug. 6, 2001, issued in PCT/SE00/02674 which is counterpart to USPN 6,903,120.

International Search Report and International Preliminary Examination Report dated Oct. 29, 2001, issued in PCT/SE00/02673 which is counterpart to U.S. Appl. No. 10/168,297.

Morita, et al., "Practical Application of the Palladium–catalyzed Amination in Phenylpiperazine Synthesis: An Efficient Synthesis of a Metabolite of the Antipsychotic Agent Aripiprazole", *Tetrahedron,* May 7, 1998, pp. 4811–4818, vol. 54, No. 19, Pergamon, Elsevier Science Ltd., Oxford, England & NY, USA.

Oshiro, et al., "Novel Antisychotic Agents with Dopamine Autoreceptor Agonist Properties: Synthesis and Pharmacology of 7–[4–Phenyl–1–piperazinyl)butoxyl]–3,4–dihydro–2(1H)–quinolinone Derivatives", *J. Med.Chem.,* 1998, pp. 658–667, vol. 41, American Chemical Society, Washington, DC.

Manoury, et al., "Synthesis and Analgesic Activities of Some (4–Substituted phenyl–1–piperazinyl)alkyl 2–Aminobenzoates and 2–Aminocotinates", *Journal of Medicinal Chemistry,* 1979, pp. 554–559, vol. 22, No. 5, Amerian Chemical Society, Washington, DC.

Patent Family Reference to U.S. Pat. No. 1,459,013 and English Abstracts.

Patent Family Reference to WO 1997/003986 and English Abstracts.

MODULATORS OF DOPAMINE NEUROTRANSMISSION

Matter enclosed in heavy brackets [ ] appears in the original patent but forms no part of this reissue specification; matter printed in italics indicates the additions made by reissue.

FIELD OF THE INVENTION

The present invention relates to new modulators of dopamine neurotransmission, and more specifically to new substituted 4-(phenyl N-alkyl)-piperazines and 4-(phenyl N-alkyl)-piperidines, and use thereof.

BACKGROUND OF THE INVENTION

Dopamine is a neurotransmitter in the brain. Since this discovery, made in the 1950s, the function of dopamine in the brain has been intensely explored. To date, it is well established that dopamine is essential in several aspects of brain function including motor, cognitive, sensory, emotional and autonomous (e.g. regulation of appetite, body temperature, sleep) functions. Thus, modulation of dopaminergic function may be beneficial in the treatment of a wide range of disorders affecting brain functions. In fact, both neurologic and psychiatric disorders are treated with medications based on interactions with dopamine systems and dopamine receptors in the brain.

Drugs that act, directly or indirectly, at central dopamine receptors are commonly used in the treatment of neurologic and psychiatric disorders, e.g. Parkinson's disease and schizophrenia. Currently available dopaminergic pharmaceuticals have severe side effects, such as extrapyramidal side effects and tardive dyskinesia in dopaminergic antagonists used as antipsychotic agents, and dyskinesias and psychoses in dopaminergic agonists used as anti-Parkinson's agents. Therapeutic effects are unsatisfactory in many respects. To improve efficacy and reduce side effects of dopaminergic pharmaceuticals, novel dopamine receptor ligands with selectivity at specific dopamine receptor subtypes or regional selectivity are sought for. In this context, also partial dopamine receptor agonists, i.e. dopamine receptor ligands with some but not full intrinsic activity at dopamine receptors, are being developed to achieve an optimal degree of stimulation at dopamine receptors, avoiding excessive dopamine receptor blockade or excessive stimulation.

Compounds belonging to the class of substituted 4-phenyl-N-alkyl)piperazine and substituted 4-(phenyl-N-alkyl)piperidines have been previously reported. Among these compounds, some are inactive in the CNS, some display serotonergic or mixed serotonergic/dopaminergic pharmacological profiles, while some are full or partial dopamine receptor antagonists or agonists with high affinity for dopamine receptors.

A number of 4-phenylpiperazines and 4-phenylpiperidine derivatives are known and described, for example Costall et al. European J. Pharm. 31, 94, (1975), and Mewshaw et al. Bioorg. Med. Chem. Lett., 8, 295, (1998). The reported compounds are substituted 4-phenyl-piperazines, most of them being 2-, 3- or 4-OH phenyl substituted and displaying DA autoreceptor agonist properties.

Fuller R. W. et al., J. Pharmacol. Exp. Therapeut. 218, 636, (1981) disclose substituted piperazines (e.g. 1-(m-trifluoromethylphenyl)piperazine) which reportedly act as serotonin agonists and inhibit serotonin uptake. Fuller R. W. et al Res., Commun. Chem. Pathol. Pharmacol. 17, 551, (1977) disclose the comparative effects on the 3,4-dihydroxyphenylacetic acid and Res. Commun. Chem. Pathol. Pharmacol. 29, 201, (1980) disclose the comparative effects on the 5-hydroxyindole acetic acid concentration in rat brain by 1-(p-chlorophenol)-piperazine.

Boissier J. et al., Chem Abstr. 61:10691c, disclose disubstituted piperazines. The compounds are reportedly adrenolytics, antihypertensives, potentiators of barbiturates, and depressants of the central nervous system. In addition, Akasaka et al (EP 0675118) disclose bifenylderivatives of piperazines, which exhibits dopamine $D_2$ receptor antagonism and/or 5-$HT_2$ receptor antagonism.

A number of different substituted piperazines have been published as ligands at 5-$HT_{1A}$ receptors, for example Glennon R. A. et al. J. Med. Chem., 31, 1968, (1988) and van Steen B. J., J. Med. Chem., 36, 2751, (1993), Dukat M.-L., J. Med. Chem., 39, 4017, (1996). Glennon R. A. discloses, in international patent applications WO 93/00313 and WO 91/09594, various amines, among them substituted piperazines, as sigma receptor ligands. Clinical studies investigating the properties of sigma receptor ligands in schizophrenic patients have not generated evidence of antipsychotic activity, or activity in any other CNS disorder. Two of the most extensively studied selective sigma receptor antagonists, BW234U (rimcazole) and BMY14802, have both failed in clinical studies in schizophrenic patients (Borison et al, 1991, Psychopharmacol Bull 27(2): 103-106; Gewirtz et al, 1994, Neuropsychopharmacology 10:37-40).

SUMMARY OF THE INVENTION

Among the compounds belonging to the class of substituted 4-(phenyl-N-alkyl)piperazine and substituted 4-phenyl-N-alkyl)piperidines previously reported some are inactive in the CNS, some display serotonergic or mixed serotonergic/dopaminergic pharmacological profiles while some are full or partial dopamine receptor antagonists with high affinity for dopamine receptors.

The object of the present invention is to provide new pharmaceutically active compounds, especially useful in treatment of disorders in the central nervous system, which do not have the disadvantages of the above described substances.

In the work leading to the present invention, it was found that it is desired to provide substances with specific pharmacological properties, namely modulating effects on dopamine neurotransmission. These properties have not been described earlier, and they are not possible to obtain with the earlier known compounds.

The compounds of the present invention have unexpectedly been found to act preferentially on dopaminergic systems in the brain. They have effects on biochemical indices in the brain with the characteristic features of dopamine antagonists, e.g. producing increases in concentrations of dopamine metabolites.

Yet, dopamine receptor antagonists characteristically suppress behavioral activity across a variety of experimental settings including spontaneous locomotion, amphetamine induced hyperactivity. They are also known to induce catalepsy in rodents. In contrast, the compounds of this invention show no or limited inhibitory effects on locomotor activity. Although some of the compounds can reduce locomotion, they do not induce the profound behavioral inhibition, characteristic of dopamine $D_2$ receptor antagonists. The compounds of this invention either lack inhibitory effects on locomotor activity, or exert milder inhibitory effects on locomotor activity than what would be expected from dopaminergic antagonists. Further, they can even be mild stimulants on behavior. Despite their behavioral stimulant properties some of the compounds can reduce d-amphetamine induced hyperactivity.

Thus, the compounds of this invention surprisingly show a dopaminergic action profile with clear antagonist like effects on brain neurochemistry but no, or mild, antagonist like effects, on normal behavior, they can activate animals with a low baseline activity, but can also inhibit behavior in states of hyperactivity. The action profile suggests modulatory effects on dopaminergic functions, clearly different from known compounds belonging to these chemical classes or effects anticipated of typical dopamine receptor antagonists or agonists from these or other chemical classes.

Given the involvement of dopamine in a large variety of CNS functions and the clinical shortcomings of presently available pharmaceuticals acting on dopamine systems, the novel class of dopaminergic modulators presented in this invention may prove superior to presently known dopaminergic compounds in the treatment of several disorders related to dysfunctions of the CNS, in terms of efficacy as well as side effects.

Some compounds of this invention have been found to have surprisingly good pharmacokinetic properties including high oral bioavailability. They are thus suitable for the preparation of orally administered pharmaceuticals. There is no guidance in the prior art how to obtain compounds with this effect on dopamine systems in the brain.

The present invention relates to new di-substituted 4-(phenyl-N-alkyl)-piperazines and di-substituted 4-(phenyl-N-alkyl)-piperidines in the form of free base or pharmaceutically acceptable salts thereof, process for their preparation, pharmaceutical compositions containing said therapeutically active compound and to the use of said active compound in therapy. An objective of the invention is to provide a compound for therapeutic use, and more precisely a compound for modulation of dopaminergic systems in the mammalian brain including man. It is also an objective of the invention to provide a compound with therapeutic effects after oral administration.

More precisely, the present invention is directed toward substituted 4-(phenyl N-alkyl)-piperazine or 4-(phenyl-N-alkyl)-piperidine compounds of Formula 1:

(1)

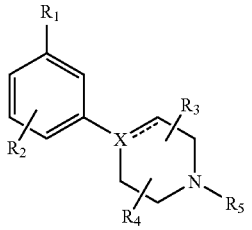

wherein:

X is selected from the group consisting of N, CH, and C, however X may only be C when the compound comprises a double bind at the dotted line;

$R_1$ is selected from the group consisting of $CF_3$, $OSO_2CF_3$, $OSO_2CH_3$, $SOR_7$, $SO_2R_7$, $COR_7$, CN, $OR_3$, $NO_2$, $CONHR_3$, 3-thiophene, 2-thiophene, 3-furane, 2-furane, F, Cl, Br, and I, wherein $R_7$ is as defined below;

$R_2$ is selected from the group consisting of F, Cl, Br, I, CN, $CF_3$, $CH_3$, $OCH_3$, OH, and $NH_2$;

$R_3$ and $R_4$ are independently selected from the group consisting of H and $C_1$-$C_4$ alkyls;

$R_5$ is selected from the group consisting of $C_1$-$C_4$ alkyls, allyls, $CH_2SCH_3$, $CH_2CH_2OCH_3$, $CH_2CH_2CH_2F$, $CH_2CF_3$, 3,3,3-trifluoropropyl, 4,4,4-trifluorobutyl, and —$(CH_2)$—$R_6$, wherein $R_6$ is as defined below;

$R_6$ is selected from the group consisting of $C_3$-$C_6$ cycloalkyls, 2-tetrahydrofurane, and 3-tetrahydrofurane;

$R_7$ is selected from the group consisting of $C_1$-$C_3$ alkyls, $CF_3$, and $N(R_4)_2$, wherein $R_4$ is as defined above, and pharmaceutically acceptable salts thereof.

The compounds according to this invention possess dopamine modulating properties and are useful in treating numerous central nervous system disorders including both psychiatric and neurological symptoms. Diseases in which compounds with modulating effects on dopaminergic systems may be beneficial are in disorders related to aging, for preventing bradykinesia and depression and for the improvement of mental functions. They may also be used to ameliorate symptoms of mood disorders. They may be used in obesitas as an anorectic agent and in other eating disorders. They may be used to improve cognitive functions and related emotional disturbances in neurodegenerative disorders as well as after brain damage induced by vascular or traumatic insults. Likewise, cognitive and motor dysfunctions associated with developmental disorders appearing in infancy, childhood, or adolescence may improve. They can be used to improve all symptoms of schizophrenia and schizophreniform disorders, to improve ongoing symptoms as well as to prevent the occurrence of new psychotic episodes. Other psychotic disorders not characterized as schizophrenia, schizoaffective syndromes as well as psychotic symptoms, delusions and hallucinations induced by other drugs may also improve. Disruptive behavior disorders such as attention deficit hyper activity disorder (ADHD), conduct disorder and oppositional defiant disorder may also improve. They can also be used in tic disorders such as Gilles de la Tourette's syndrome and other tic disorders. Also, speech disorders such as stuttering may improve. They may also be for regulating pathological disorders of food, coffee, tea, tobacco, alcohol and addictive drug intake and also to improve mental disorders associated with psychoactive substance overuse (including alcohol) including hallucinations, withdrawal symptoms, delusions, mood disorders, sexual and cognitive disturbances.

Anxiety disorders, obsessive-compulsive disorder and other impulse control disorders, post traumatic stress syndrome, personality disorders, and conversion hysteria may also be treated with the compounds in the invention. Other indications include sleep disorders, "jet lag" and disorders of sexual functions.

Neurological indications include the treatment of Huntington's disease, movement disorders such as dyskinesias including other choreas as well as primary, secondary and paroxysmal dystonias, tardive movement disorders such as tardive dyskinesia and tardive dystonia as well as other drug induced movement disorders. Restless legs, periodic leg movements and narcolepsy may also be treated with compounds included in the invention. They may also improve mental and motor function in Parkinson's disease, and in related parkinsonian syndromes such as multiple system atrophies, progressive supranuclear palsy, diffuse Lewy body disorder and vascular parkinsonism. They may also be used to ameliorate tremor of different origins.

The compounds in the invention can also be used for the treatment of vascular headaches such as migraine and cluster headache, both as acute and prophylactic treatment. They may improve rehabilitation following vascular or traumatic brain injury. Moreover, they may be used to relieve pain in conditions characterized by increased muscle tone.

DETAILED DESCRIPTION OF THE INVENTION

Pharmacology

Evidence is available that neurotransmission in the CNS is disturbed in psychiatric and neurologic diseases. In many instances, for example in schizophrenia or Parkinson's disease, pharmacotherapies based on antagonism or agonism at dopamine receptors are useful, but not optimal, In recent years much efforts have been put on finding novel and selective ligands for dopamine receptor subtypes ($D_1$, $D_2$, $D_3$, $D_4$, $D_5$) with the aim to improve efficacy and reduce side effects.

The present invention offers another principle for novel therapeutics based on interactions with dopamine systems. The compounds of this invention have effects on brain neurochemistry similar to antagonists at dopamine $D_2$ receptors. In contrast to currently used dopamine receptor antagonists the compounds of this invention show no, or limited inhibitory effects on locomotion. They can even be mildly activating. Surprisingly, the compounds of the invention can actually also reduce the increase in activity induced by direct or indirect dopaminergic agonists, i.e. d-amphetamine and congeners. Furthermore, some of the compounds display a high oral bioavalability.

Below, some examples of preferred compounds according to the invention are discussed more in detail.

One preferred compound is 4-(4-chloro-3-trifluoromethyl-phenyl)-1-propyl-piperidine, further illustrated in Example 9. In rat, 4-(4-chloro-3-trifluoromethyl-phenyl)-1-propyl-piperidine increases 3,4-dihydroxyphenyl-acetic acid in the striatum from 1089±102 (controls) to 1680±136 ng/g tissue, $p<0.05$, n=4, at 50 μmol/kg s.c. Surprisingly, it has no significant inhibition on spontaneous behavior; 1287±272 cm/30 min (for controls) vs. 944±114 cm/30 min at 50 μmol/kg s.c. Nor did it affect the locomotor activity of habituated rats, from 1381±877 cm/60 min (for the controls) to 1300±761 cm/60 min at 50 μmol/kg s.c.

d-Amphetamine induced hyperactivity was significantly reduced from 8376±2188 cm/30 min, to 3399±1247 cm/30 min, at 50 μmol/kg s.c., $p<0.05$, n=4, Fischer PLSD. Surprisingly, 4-(4-chloro-3-trifluoromethyl-phenyl)-1-propyl-piperidine has an oral availability (F) of 55% in rat.

Similar to 4-(4-chloro-3-trifluoromethyl-phenyl)-1-propyl-piperidine, 4-(4-fluoro-3-trifluoromethylphenyl)-1-propyl-piperidine, which the compound according to Example 43, increases 3,4-dihydroxyphenyl-acetic acid in the striatum from 974±39 (for controls) to 1895±100 ng/g tissue, $p<0.05$, n=4, at 100 μmol/kg s.c. According to the behavioral assay in nonpretreated rats it mildly increases locmotoractivity from 14±4 cm/30 min (for the controls) to 540±128 cm/30 min, 30-60 min, $p<0.05$, n=4, at 100 μmol/kg s.c. Thus, 4-(4-fluoro-3-trifluoromethylphenyl)-1-propyl-piperidine displays the properties desired according to the present invention.

The importance of the substitution in the para position is demonstrated by 1-propyl-4-(3-triflouromethyl-phenyl) piperazine, which is not a compound according to the present invention, which carries the same substituent as 4-(4-chloro-3-trifluoromethyl-phenyl)-1-propyl-piperidene (the compound of Example 9) in the meta position but lacks substitution in the para position. With this change the neurochemical effects are retained but the effects on behavior are significantly altered. Thus, 1-propyl-4-(3-trifluoromethyl-phenyl)-piperazine increases 3,4-dihydroxyphenyl-acetic acid in the striatum from 1066±46 (controls) ng/g tissue to 3358±162 ng/g tissue at 50 μmol/kg s.c., $p<0.05$, n=4, followed by behavioral inhibition from 1244±341 cm/60 min (controls) to 271±137 at 50 μmol/kg s.c., $p<0.05$, n=4. These properties are not desired according to the present invention, and accordingly 1-propyl-4-(3-trifluoromethyl-phenyl)-piperazine is not a substance according to the present invention. 1-propyl-4-(3-trifluoromethyl-phenyl)-piperazine has an oral availability (F) of 9,5% in rat.

1-(4-Chloro-3-nitro-phenyl)-4-propyl-piperazine, which is the compound of Example 19, increases 3,4-dihydroxyphenyl-acetic acid in the striatum from 1074±42 (for controls) to 1693±104 ng/g tissue, $p<0.05$, n=4, at 100 μmol/kg s.c. According to the behavioral assay it mildly increases locomotoractivity from 56±25 cm/30 min (for the controls) to 266±89 cm/30 min, 30-60 min, $p=0.06$, n=4, at 100 μmol/kg s.c. 1-(4-Chloro-3-nitro-phenyl)-4-propyl-piperazine reduces d-amphetamine induced hyperactivity from 29792±3212 cm/60 min (d-amphetamine controls) to 3767±2332 cm/60min, $p<0.05$, n=4, at 100 μmol/kg s.c. Thus, 1-(4-Chloro-3-nitro-phenyl)-4-propyl-piperazine shows the desired properties.

cis-4-(4-Fluoro-3-trifluoromethyl-phenyl)-2,6-dimethyl-1-propyl-piperazine, which is the compound according to Example 34, has the ability to increase spontaneous behavior in the habituated rat; from 415±214 cm/60 min (for controls) to 919±143 cm/60 min, $p=0.056$, n=4, at 33 μmol/kg s.c. in combination with a slight increase in 3,4-dihydroxyphenyl-acetic acid in the striatum from 1015±61 (for controls) to 1278±143 ng/g tissue, $p=0.13$, n=4, at 33 μmol/kg s.c.

The ability to inhibit d-amphetamine induced hyperactivity is demonstrated by cis-4-(3,4-dichloro-phenyl)-2,6-dimethyl-1-propyl-piperazine, which is the compound of Example 35. d-Amphetamine induced hyperactivity is reduced from 19595±2999 cm/60 min (for d-amphetamine controls) to 6514±3374 cm/60 min, $p<0.05$, n=4, at 100 μmol/kg s.c.

The compounds according to the invention are especially suitable for treatment of disorders in the central nervous system, and particularly for treatment of dopamine mediated disorders. They may, e.g. used to ameliorate symptoms of mood disorders, in obesitas as an anorectic agent and in other eating disorders, to improve cognitive functions and related emotional disturbances, to improve cognitive and motor dysfunctions associated with developmental disorders, to improve all symptoms of psychosis, including schizophrenia and schizophreniform disorders, to improve ongoing symptoms as well as to prevent vent the occurrence of new psychotic episodes, to regulate pathological disorders due to intake of food, coffee, tea, tobacco, alcohol and addictive drugs etc.

The compounds according to the invention can thus be used to treat symptoms in e.g.:

schizophrenia and other psychotic disorders, such as catatonic disorganized, paranoid, residual, or differentiated schizophrenia; schizophreniform disorder; schizoaffective disorder; delusional disorder; brief psychotic disorder; shared psychotic disorder; psychotic disorder due to a general medical condition with delusions and/or hallucinations;

mood disorders, such as depressive disorders, e.g., dysthymic disorder or major depressive disorder; bipolar disorders, e.g., bipolar I disorder, bipolar II disorder, and cyclothymic disorder; mood disorder due to a general medical condition with depressive, and/or manic features; and substance-induced mood disorder;

anxiety disorders, such as acute stress disorder, agoraphobia without history of panic disorder, anxiety disorder due to general medical condition, generalized anxiety disorder, obsessive-compulsive disorder, panic disorder with agoraphobia, panic disorder without agoraphobia, post-traumatic stress disorder, specific phobia, social phobia, and substance-induced anxiety disorder;

eating disorders, such as anorexia nervosa, bulimia nervosa, and obesitas;

sleep disorders, such as dyssomnias, e.g., breathing-related sleep disorder, circadian rhythm sleep disorder, hypersomnia, insomnia, narcolepsy, and "jet lag";

impulse-control disorders not elsewhere classified, such as intermittent explosive disorder, kleptomania, pathological gambling, pyromania, and trichotillomania;

personality disorders, such as paranoid, schizoid or schizotypal disorder; antisocial, borderline, histrionic, and narcissistic disorder; and avoidant, dependent, obsessive-compulsive disorder;

medication-induced movement disorders, such as neuroleptic induced parkinsonism, neuroleptic malignant syndrome, neuroleptic induced acute and tardive dystonia, neuroleptic induced akathisia, neuroleptic induced tardive dyskinesia, medication induced tremor, and medication induced dyskinesias;

substance-related disorders, such as abuse, dependence, anxiety disorder, intoxication, intoxication delirium, psychotic disorder, psychotic disorder with delusions, mood disorder, persisting amnestic disorder, persisting dementia, persisting perception disorder, sexual dysfunction, sleep disorder, withdrawal, and withdrawal delirium due to use ore misuse of alcohol, amphetamine (or amphetamine-like substances), caffeine, cannabis, cocaine, hallucinogens, inhalants, nicotine, opioids, phencyclidine (or phencyclidine-like substances), sedative substances, hypnotic substances, and/or anxiolytic substances;

disorders usually first diagnosed in infancy, childhood, or adolescence, such as mental retardation; learning disorders; motor skills disorders, e.g. developmental coordination disorder; communication disorders, e.g. expressive language disorder, phonological disorder, receptive-expressive language disorder and stuttering; pervasive developmental disorders, e.g. Asperger's disorder, autistic disorder, childhood disintegrative disorder, and Rett's disorder; attention-deficit and disruptive behavior disorders, e.g. attention-deficit/hyperactivity disorder, conduct disorder, and oppositional defiant disorder; feeding and eating disorders of infancy or early childhood, e.g. feeding disorder of infancy or early childhood, pica, rumination disorder; tic disorders, e.g. chronic motor or vocal tic disorder, and Tourette's disorder; other disorders of infancy, childhood, or adolescence, e.g. selective mutism, and stereotypic movement disorder;

delirium, dementia, amnestic and other cognitive disorders, such as Alzheimer's, Creutzfeidt-Jakob disease, dead trauma, Huntington's disease, HIV disease, Pick's disease, and diffuse Lewy body dementia;

conversion hysteria;

conditions connected to normal aging, such as disturbances in motor functions and mental functions;

Parkinson's Disease and related disorders, such as multiple system atrophies, e.g. striatonigral degeneration, olivopontocerebellar atrophy, and shydrager syndrome; progressive supranuclear palsy; corticobasal degeneration; and vascular parkinsonism;

tremors, such as essential, orthostatic, rest, cerebellar, and secondary tremor headaches, such as migraine, cluster headache, tension type headache, and paroxysmal headache;

movement disorders, such as dyskinesias, e.g. in deneral medicine condition, secondary to trauma or vascular insult, hemiballism, athetosis, Sydenham's chorea, and paroxysmal; dystonias; Ekbom's syndrome (restless legs); Wilson's Disease; Hallerworden-Spatz disease;

rehabilitation medicine, e.g. to improve rehabilitation after vascular or traumatic brain injury;

pain in conditions characterized by increased muscular tone, such as fibromyalgia, myofascial syndrome, dystonia, and parkinsonism; as well as conditions related to the above that fall within the larger categories but does not meet the criteria of any specific disorder within those categories.

Synthesis

The synthesis of the present compounds is carried out by methods that are conventional for the synthesis of related known compounds. The syntheses of compounds in Formula 1, in general, comprise the reaction of an intermediate that supplies the alkyl group with an intermediate piperidine or piperazine that supplies the amine group of Formula 2:

(2)

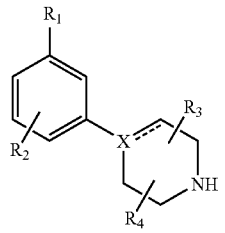

A convenient method of synthesis of the present compounds is by use of an alkyl iodide (e.g. 1-propyl-iodide). Alternatively, other leaving groups besides iodide may be used on the alkyl group, of course, such as sulfonates, particularly methanesulfonate or toluenesulfonate, bromo and the like. The alkyl intermediate is reacted with the appropriate amine in the presence of any convenient acid scavenger. The usual bases such as alkali metal or alkaline earth metal carbonates, bicarbonates and hydroxides are useful acid scavengers, as are some organic bases such as trialkylamines and trialkanolamines. The reaction medium for such reactions may be any convenient organic solvent which is inert to the basic conditions; acetonitrile, esters such as ethylacetate and the like and halogenated alkane solvents are useful. Usually the reactions will be carried out at elevated temperatures such as from ambient temperature to the reflux temperature of the reaction mixture, particularly from 50° C. to about 100° C.

Another convenient method of synthesis of the present compounds involves reductive amination with an amine of Formula 2:

(2)

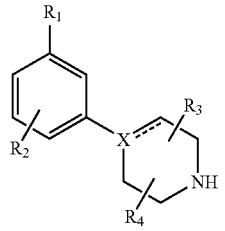

with an aldehyde or ketone, either in the presence of a reducing agent such as sodium cyanoborohydride or sodium triacetoxyborohydride or followed by reduction, e.g. using catalytic hydrogenation, to give a corresponding compound of Formula 1.

Compounds of Formula 3:

(3)

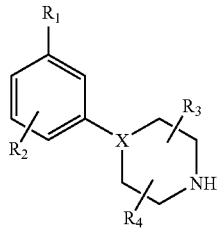

wherein X═N is accomplished by reacting compounds of Formula 4:

(4)

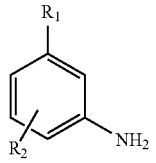

with compounds of Formula 5:

(5)

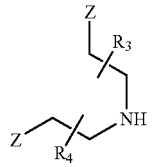

where Z is a leaving group like iodide. Other leaving groups besides iodide may be used on the alkylgroup, of course, such as sulfonates, particularly methanesulfonate or toluenesulfonate, bromo and the like. The alkyl intermediate is reacted with the appropriate amine in the presence of any convenient acid scavenger. The usual bases such as alkali metal or alkaline earth metal carbonates, bicarbonates and hydroxides are useful acid scavengers, as are some organic bases such as trialkylamines and trialkanolamines. The reaction is performed in a suitable solvent such as n-butanol by heating at about 50-150° C.

Compounds of the Formula 1 wherein X═N is also accomplished by reacting compounds of Formula 6:

(6)

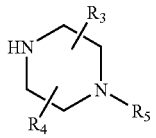

with an aryl substituted with a leaving group of Formula 7:

(7)

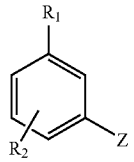

where Z is halide e.g. chloro, bromo, iodo, or sulfonate e.g. —$OSO_2CF_3$, or —$OSO_2F$, in the presence of a base and a zerovalent transition metal catalyst such as Pd or Ni, according to known method (Tetrahedron Letters, vol 37, 1996, 4463-4466, J. Org. Chem., vol. 61, 1996, 1133-1135).

The catalyst, preferably Pd will have the ability to form ligand complex and undergo oxidative addition. Typical Pd catalysts will be $Pd_2(dba)_3$ (wherein dba refers to di-benzylidene acetone), $Pd(PPh_3)_4$, $Pd(OAc)_2$, or $PdCl_2[P(o\text{-}tol)_3]_2$ and typical phosphine ligands will be BINAP, $P(o\text{-}tol)_3$, dppf, or the like. The usual bases such as alkali metal or alkaline earth metal carbonates, bicarbonates and alkyloxides are useful acid scavengers, as are some organic bases such as trialkylamines and trialkanolamines. The reaction medium for such reactions may be any convenient organic solvents, which are inert to the basic conditions; acetonitrile, toluene, dioxane, NMP (N-methyl-2-pyrrolidone), DME (dimethoxyethane), DMF (N,N-dimethylformamide), DMSO (dimethylsulfoxide) and THF (tetrahydrofuran) solvents are useful. Usually the reactions will be carried out at elevated temperatures such as from ambient temperature to the reflux temperature of the reaction mixture, particularly from 50° C. to about 120° C.

Compounds of the Formula 1 wherein X═N is also accomplished by reacting compounds of Formula 6 with an aryl substituted with a leaving group (e.g. F or Cl) via nucleophilic aromatic displacement reactions in the presence of a base as explained above.

Compounds of the Formula 1 wherein X═CH or C is also accomplished by transition metal catalyzed cross-coupling reaction, known as, for example, Suzuki and Stille reactions, to those skilled in the art.

The reaction may be carried out between compounds of Formula 8:

(8)

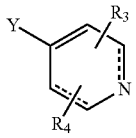

wherein Y is, for example, a dialkylborane, dialkenylborane or boronic acid (e.g. $BEt_2$, $B(OH)_2$) or a trialkyltin (e.g. $SnMe_3$, SnBu3), and an aryl substituted with a leaving group of Formula 7:

(7)

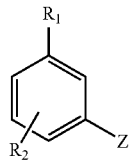

(for definition of Z, see above) in the presence of a base and a zerovalent transition metal catalyst such as Pd or Ni, according to known methods (Chem. Pharm. Bull., vol 33, 1985, 4755-4763, J. Am. Chem. Soc., vol. 109, 1987, 5478-5486., Tetrahedron Lett., vol. 33, 1992, 2199-2202). In addition, Y can also be a zink- or magnesium-halide group (e.g. $ZnCl_2$, $ZnBr_2$, $ZnI_2$, MgBr, MgI) according to known methods (Tetrahedron Lett., vol. 33, 1992, 5373-5374, Tetrahedron Lett., vol. 37, 1996, 5491-5494).

The catalyst, preferably Pd will have the ability to form ligand complex and undergo oxidative addition. The definition of ligands, bases and solvents, is mentioned above.

Alternatively, the transition metal catalyzed cross-coupling coupling reaction can be performed with the opposite substitution pattern: (9)

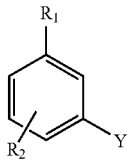

with an heteroaryl/alkenyl substituted with an leaving group of Formula 10: (10)

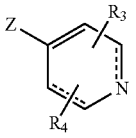

in the presence of a base and a zerovalent transition metal catalyst such as Pd or Ni, according known methods discussed in the previous paragraph.

Compounds of Formula 11: (11)

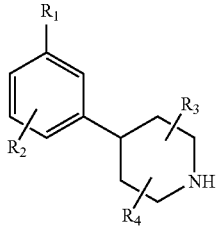

can be prepared by catalytic hydrogenation of the tetrahydropyridine or pyridine from the previous paragraph, using standard methods known in the art, generally with palladium on carbon, $PtO_2$, or Raney nickel as the catalyst. The reaction is performed in an inert solvent, such as ethanol or ethyl acetate, either with or without a protic acid, such as acetic acid or HCl. When the pyridine ring is quaternized with an alkyl group the ring can be partly reduced by $NaBH_4$ or $NaCNBH_4$, yielding the tetrahydropyridine analog which can further be reduced with catalytic hydrogenation.

Another convenient method of syntheses of compounds of the Formula 1, wherein X═CH or C is also accomplished by treating arylhalides of Formula 7: (7)

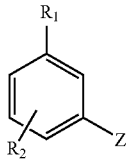

wherein Z is Cl, Br, or I, with alkyllithium reagents, for example, butyllithium, sec-butyllithium or tert-butyllithium, preferably butyllitium or Mg (Grignard reaction) in an inert solvent. Suitable solvents include, for example ether or tetrahydrofuran, preferably tetrahydrofuran. Reaction temperatures range from about −110° C. to about 0° C. The intermediate lithium anions or magnesium anions thus formed may then be further reacted with a suitable electrophile of Formula 12: (12)

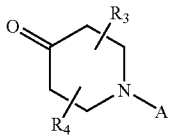

wherein A is defined as a protecting group like t-Boc (tert-butoxycarbonyl), Fmoc (fluorenylmethoxycarbonyl), Cbz (benzyloxycarbonyl) or an alkylgroup like benzyl. The intermediates of formula 13: (13)

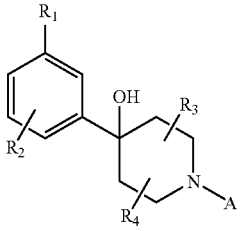

which are formed require that the hydroky group be removed so as to result in compounds of Formula 1 (X═CH or C). This step may be accomplished by one of several standard methods known in the art. For example, a thiocarbonyl derivative (for example a xanthate) may be prepared and removed by a free radical process, of which are known to those skilled in the art. Alternatively, the hydroxyl group may be removed by reduction with a hydride source such as triethylsilane under acidic conditions, using such as, for example, trifluoroacetic acid or boron trifluoride. The reduction reaction can be performed neat or in a solvent, such as methylene chloride. A further alternative would be to first convert the hydroxyl group to a suitable leaving group, such as tosylate or chloride, using standard methods. The leaving group is then removed with a nucleophilic hydride, such as, for example, lithium aluminium hydride. This last reaction is performed typically in an inert solvent, such as, ether or tetrahydrofuran.

Another alternative method for removing the hydroxyl group is to first dehydrate the alcohol to an olefin with a reagent such as Burgess salt (J. Org. Chem., vol 38, 1973, 26) followed by catalytic hydrogenation of the double bond under standard conditions with a catalyst such as palladium on carbon. The alcohol may also be dehydrated to the olefin by treatment with acid such as p-toluenesulfonic acid or trifluoroacetic acid.

The protecting group, A, is removed under standard conditions known by those skilled in the art. For example, t-Boc cleavages are conveniently carried out with trifluoroacetic acid either neat or in combination with methylene chloride. F-moc is conveniently cleaved off with simple bases such as, ammonia, piperidine, or morpholine, usually in polar solvents such as DMF and acetonitrile. When A is Cbz or benzyl, these are conveniently cleaved off under catalytic hydrogenation conditions. The benzyl group can also be cleaved off under N-dealkylation conditions such as treatment with α-chloroethyl chloroformate (J. Org. Chem., vol 49, 1984, 2081-2082).

It is further possible to convert a radical R1 in a compound of the Formula 1 into another radical R1, e.g. by oxidizing methylsulfide to methylsulfone (for example by m-chloroperoxybenzoic acid), substitution of a triflate or halide group with a cyano group (for example palladium catalyzed cyanation), substitution of triflate or halide group with a ketone (for example palladium catalyzed Heck reaction with butyl vinyl ether), substitution of a triflate or halide group with a carboxamide (for example, palladium catalyzed carbonylation), or cleaving an ether by, for example, converting a methoxy group into the corresponding hydroxyl derivate, which can further be converted into the corresponding mesylate or triflate. The terms mesylate and triflate refers to $OSO_2CH_3$, $CH_3SO_3$ or $OSO_2CF_3$, $CF_3SO_3$, respectively.

In summary, the general process for preparing the present compounds has six main variations, which may briefly be described as follows:
Scheme 1:
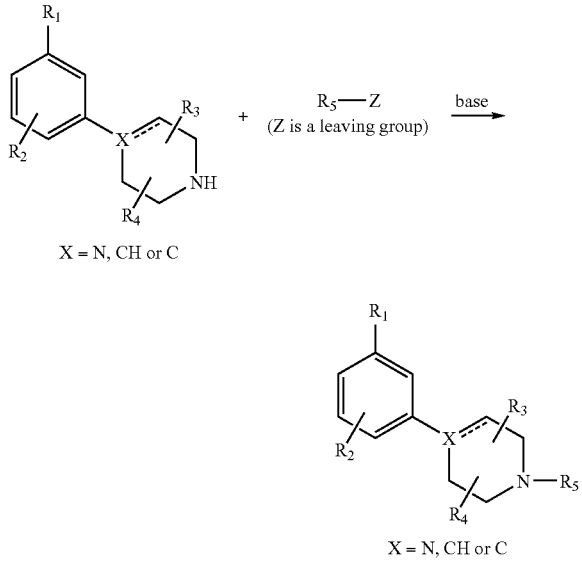
or according to Scheme 2:
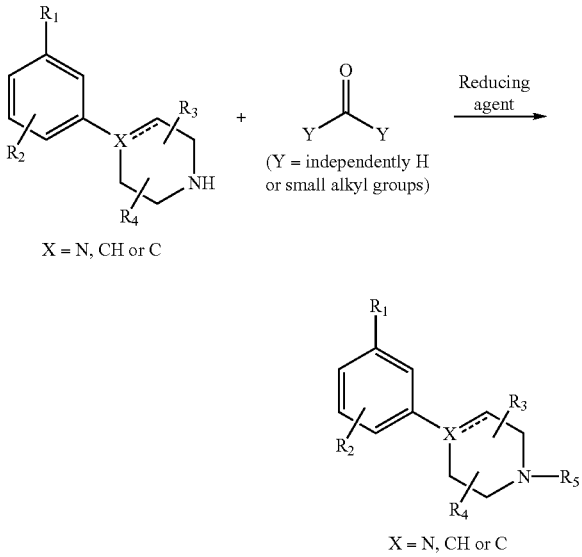
or according to Scheme 3:
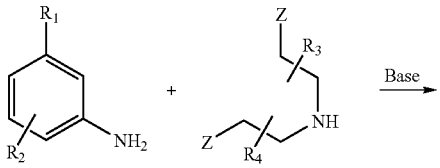
-continued
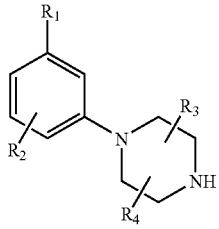
or according to Scheme 4:
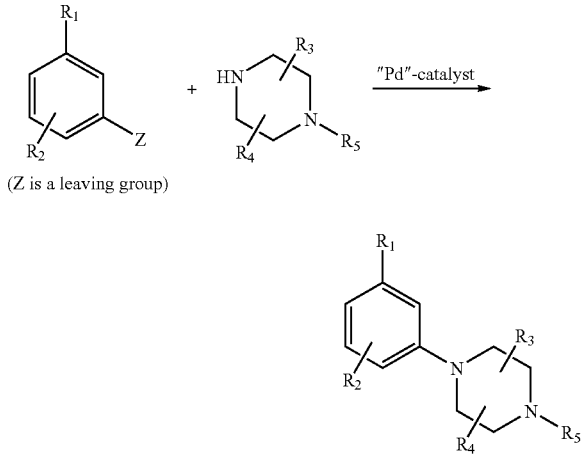
or according to Scheme 5:
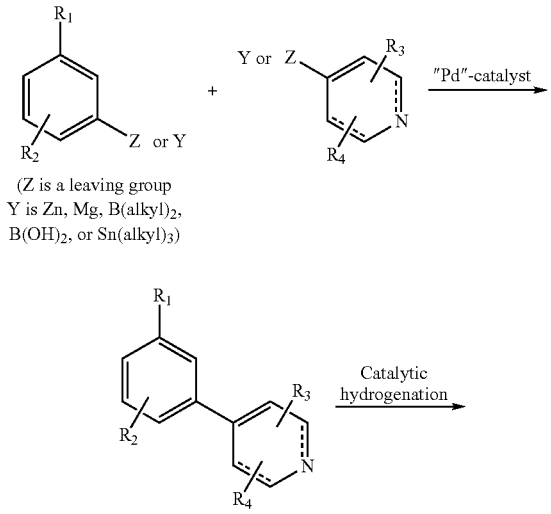

or according to Scheme 6:

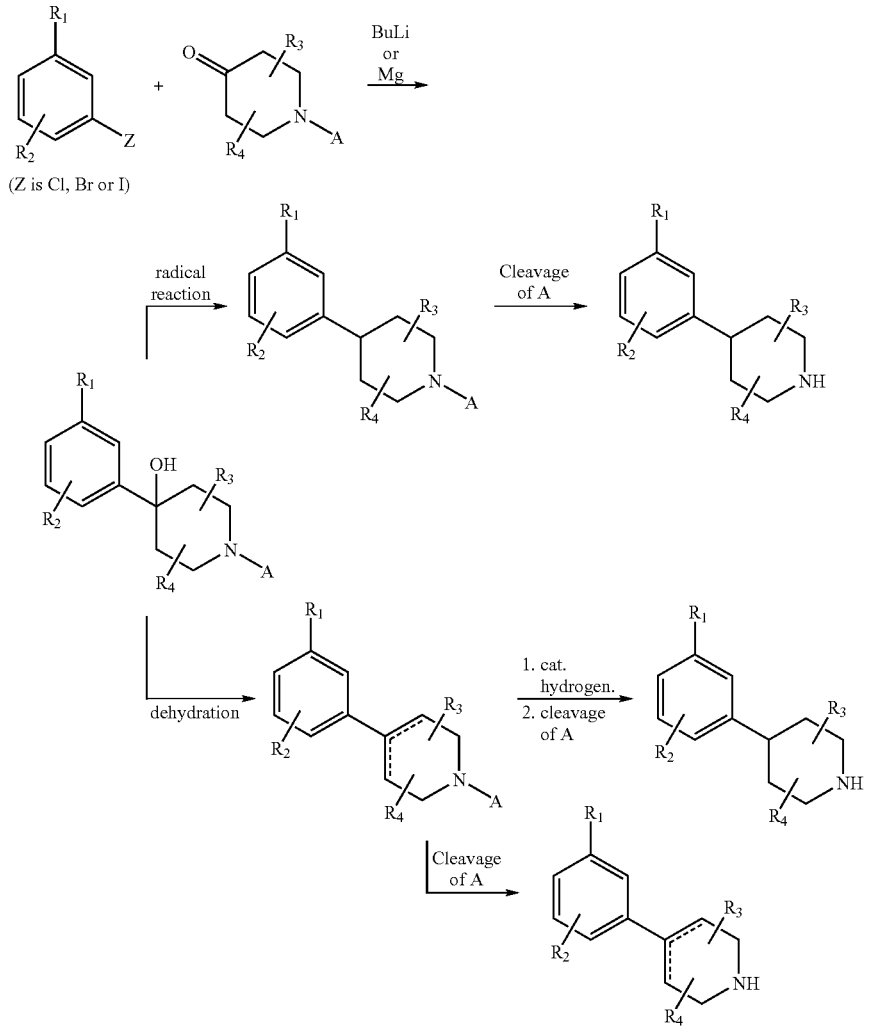

As used herein the term $C_1$-$C_4$ alkyl refers to an alkyl containing 1-4 carbon atoms in any isomeric form. The various carbon moieties are defined as follows: Alkyl refers to an aliphatic hydrocarbon radical and includes branched or unbranched forms such as methyl, ethyl, n-propyl, i-propyl, n-butyl, i-butyl, s-butyl, t-butyl. The term cycloalkyl refers to a radical of a saturated cyclic hydrocarbon such as cyclopropyl, cyclobutyl, cyclopentyl, cyclohexyl.

The term "patient" used herein refers to an individual in need of the treatment and/or prevention according to the invention.

The term "treatment" used herein relates to both treatment in order to cure or alleviate a disease or a condition, and to treatment in order to prevent the development of a disease or a condition. The treatment may either be performed in an acute or in a chronic way.

Both organic and inorganic acids can be employed to form non-toxic pharmaceutically acceptable acid addition salts of the compounds of this invention. Illustrative acids are sulfuric, nitric, phosphoric, hydrochloric, citric, acetic, lactic, tartaric, palmoic, ethane disulfonic, sulfamic, succinic, cyclohexylsulfamic, fumaric, maleic, and benzoic acid. These salts are readily prepared by methods known in the art.

The pharmaceutical composition containing a compound according to the invention may also comprise substances used to facilitate the production of the pharmaceutical preparation or the administration of the preparations. Such substances are well known to people skilled in the art and may for example be pharmaceutically acceptable adjuvants, carriers and preservatives.

In clinical practice the compounds used according to the present invention will normally be administered orally, rectally, or by injection, in the form of pharmaceutical preparations comprising the active ingredient either as a free base or as a pharmaceutically acceptable non-toxic, acid addition salt, such as the hydrochloride, lactate, acetate, sulfamate salt, in association with a pharmaceutically acceptable carrier. The carrier may be a solid, semisolid or liquid preparation. Usually the active substance will constitute between 0.1 and 99% by weight of the preparation, more specifically between 0.5 and 20% by a weight for preparations intended for injection and between 0.2 and 50% by weight for preparations suitable for oral administration.

To produce pharmaceutical preparations containing the compound of the invention in the form of dosage units for oral application, the selected compound may be mixed with a solid excipient, e.g. lactose, saccharose, sorbitol, mannitol, starches such as potato starch, corn starch or amylopectin, cellulose derivatives, a binder such as gelatine or polyvinylpyrrolidine, and a lubricant such as magnesium stearate, calcium stearate, polyethylene glycol, waxes, paraffin, and the like, and then compressed into tablets. If coated tablets are required, the cores, prepared as described above, may be coated with a concentrated sugar solution which may contain e.g. gum arabic, gelatine, talcum, titanium dioxide, and the like. Alternatively, the tablet can be coated with a polymer known to the man skilled in the art, dissolved in a readily volatile organic solvent or mixture of organic solvents. Dyestuffs may be added to these coatings in order to readily distinguish between tablets containing different active substances or different amounts of the active compound.

For the preparation of soft gelatine capsules, the active substance may be admixed with e.g. a vegetable oil or polyethylene glycol. Hard gelatine capsules may contain granules of the active substance using either the mentioned excipients for tablets e.g. lactose, saccharose, sorbitol, mannitol, starches (e.g. potato starch, cornstarch or amylopectin), cellulose derivatives or gelatine. Also liquids or semisolids of the drug can be filled into hard gelatine capsules.

Dosage units for rectal application can be solutions or suspensions or can be prepared in the form of suppositories comprising the active substance in a mixture with a neutral fatty base, or gelatine rectal capsules comprising the active substance in admixture with vegetable oil or paraffin oil. Liquid preparations for oral application may be in the form of syrups or suspensions, for example solutions containing from about 0.2% to about 20% by weight of the active substance herein described, the balance being sugar and mixture of ethanol, water, glycerol and propylene glycol. Optionally such liquid preparations may contain coloring agents, flavoring agents, saccharine and carboxymethylcellulose as a thickening agent or other excipients known to the man in the art.

Solutions for parenteral applications by injection can be prepared in an aqueous solution of a watersoluble pharmaceutically acceptable salt of the active substance, preferably in a concentration of from 0.5% to about 10% by weight. These solutions may also containing stabilizing agents and/or buffering agents and may conveniently be provided in various dosage unit ampoules. The use and administration to a patient to be treated in the clinic would be readily apparent to an ordinary skill in the art.

Additionally, the present invention is also considered to include stereoisomers as well as optical isomers, e.g. mixtures of enantiomers as well as individual enantiomers and diastereomers, which arise as a cosequense of structural asymmetry in certain compounds of the instant series. Separation of the individual isomers is accomplished by application of various methods which are well known to practitioners in the art.

In therapeutical treatment an effective amount or a therapeutic amount of the compounds of the invention are from about 0.01 to about 500 mg/kg body weight daily, preferably 0.1-10 mg/kg body weight daily. The compounds may be administered in any suitable way, such as orally or parenterally. The daily dose will preferably be administered in individual dosages 1 to 4 times daily.

The invention is further illustrated in the examples below, which in no way are intended to limit the scope of the invention.

EXAMPLE 1

1-(4-Chloro-3-trifluoromethyl-phenyl)-4-propyl-piperazine

A mixture of 5-bromo-2-chlorobenzotrifluoride (0.2 g, 0.85 mmol), n-propyl piperazine (0.15 g, 1.17 mmol), sodium tert-butoxide (0.134 g) dppf (14 mg) and $[Pd_2(dba)_3$ (10 mg) in dioxane (5 ml) was heated under argon at 100° C. for 24 h. After cooling to room temperature, the reaction mixture was taken up in $Et_2O$ (40-50 ml) and washed with brine (15-20 ml). The organic fraction was dried ($MgSO_4$), filtered and evaporated to dryness. The crude material was purified by flash chromatography on silica gel using $CH_2Cl_2$:MeOH (9:1 (v/v)). The amine was converted into the HCl-salt and recrystallized from ethanol/diethylether; m.p. 268° C. (HCl); MS m/z (rel. intensity, 70 eV)) 307 (M+, 6), 279 (33), 277 (98), 70 (bp), 56 (40). Rf=0.35 (EtOAc)

EXAMPLE 2

1-(3-Chloro-5-trifluoromethyl-phenyl)-4-propyl-piperazine

A suspension of 1-(3-Chloro-5-trifluoromethyl-phenyl)-piperazine (100 mg) and ground $K_2CO_3$ (200 mg) was stirred in $CH_3CN$ (30 mL) at room temperature. A solution of 1-bromo-propyl (52 mg) in $CH_3CN$ (5 mL) was added dropwise. The mixture was stirred at 50° C. overnight. The reaction mixture was filtered and the volatiles were evaporated in vacuum. The oily residue was chromatographed on a silica column with MeOH: $CH_2Cl_2$ (1:9 (v/v)) as eluent. Collection of the fractions containing pure product and evaporation of the solvent afforded the title compound (85 mg). MS m/z (relative intensity, 70 eV) 306 (M+, 25), 277 (bp), 234 (23), 206 (23), 179 (23).

EXAMPLE 3

1-(3-Chloro-5-trifluoromethyl-phenyl)-4-ethyl-piperazine

Beginning with 1-(3-Chloro-5-trifluoromethyl-phenyl)-piperazine and iodoethane, the title compound was recovered by the procedure described in Example 2. MS m/z (rel. intensity, 70 eV)) 292 (M+, bp), 277 (88), 234 (33), 206 (55), 179 (49).

EXAMPLE 4

1-(3-Chloro-5-trifluoromethyl-phenyl)-4-isopropyl-piperazine

Beginning with 1-(3-Chloro-5-trifluoromethyl-phenyl)-piperazine and iso-propylbromide, the title compound was recovered by the procedure described in Example 2. MS m/z (rel. intensity, 70 eV) 306 (M+, 30), 291 (bp), 206 (25), 193 (15), 179 (20).

EXAMPLE 5

1-(4-Chloro-3-trifluoromethyl-phenyl)-4-ethyl-piperazine

Beginning with 1-(4-Chloro-3-trifluoromethyl-phenyl)-piperazine and bromo-ethane, the title compound was recovered by the procedure described in Example 2. MS m/z (rel. intensity, 70 eV) 293 (M+, 6), 292 (30), 277 (29), 57 (bp), 56 (41).

EXAMPLE 6

1-(3,5-Bis-trifluoromethyl-phenyl)-4-propyl-piperazine

Beginning with 1-(3,5-Bis-trifluoromethyl-phenyl)-4-piperazine and 1-propyliodide, the title compound was recovered by the procedure described in Example 2. m.p. 266.1 (HCl), MS m/z (rel. intensity, 70 eV) 340 (M+, 20), 311 (95), 240 (30), 70 (bp), 56 (46).

EXAMPLE 7

1-(3,5-Bis-trifluoromethyl-phenyl)-4-ethyl-piperazine

Beginning with 1-(3,5-Bis-trifluoromethyl-phenyl)-4-piperazine and iodoethane, the title compound was recovered by the procedure described in Example 2. MS m/z (rel. intensity, 70 eV) 326 (M+, 65), 311 (bp), 268 (35), 240 (70), 213 (65).

EXAMPLE 8

4-(4-Chloro-3-trifluoromethyl-phenyl)-1-butyl-piperidine

Beginning with 4-(4-Chloro-3-trifluoromethyl-phenyl)-piperidine and 1-butylbromide, the title compound was recovered by the procedure described in Example 2. MS m/z (rel. intensity, 70 eV) 319 (M+, 6), 278 (31), 277 (19), 276 (bp), 70 (30).

EXAMPLE 9

4-(4-Chloro-3-trifluoromethyl-phenyl)-1-propyl-piperidine

Beginning with 4-(4-Chloro-3-trifluoromethyl-phenyl)-piperidine and 1-propyliodide, the title compound was re-covered by the procedure described in Example 2. m.p. 218-220° C. (HCl), MS m/z (rel. intensity, 70 eV) 305 (M+, 4), 278 (35), 277 (13), 276 (bp), 70 (40).

EXAMPLE 10

4-(4-Chloro-3-trifluoromethyl-phenyl)-1-ethyl-piperidine

Beginning with 4-(4-Chloro-3-trifluoromethyl-phenyl)-piperidine and iodoethane, the title compound was recovered by the procedure described in Example 2. MS m/z (rel. intensity, 70 eV) 291 (M+, 6), 278 (29), 277 (11), 276 (bp), 70 (50).

EXAMPLE 11

1-(3,4-dichloro-phenyl)-4-propyl-piperazine

Beginning with 1-(3,4-dichloro-phenyl)-4-piperazine and iodo-propane, the title compound was recovered by the procedure described in Example 2. MS m/z (rel. intensity, 70 eV) 273 (M+, 7), 272 (37), 245 (64), 243 (bp), 70 (48).

EXAMPLE 12

1-(2-Chloro-5-trifluoromethyl-phenyl)-4-propyl-piperazine

Beginning with 1-(2-Chloro-5-trifluoromethyl-phenyl)-piperazine and 1-iodopropane, the title compound was recovered by the procedure described in Example 2. m.p. 234° C. (HCl), MS m/z (rel. intensity, 70 eV) 306 (M+, 20), 279 (34), 277 (bp), 70 (99), 56 (48).

EXAMPLE 13

2-Fluoro-5-(4-propyl-piperazin-1-yl)-benzonitrile

Beginning with 2-fluoro-5-piperazin-1-yl-benzo-nitrile and 1-iodopropane, the title compound was recovered by the procedure described in Example 2. MS m/z (rel. intensity, 70 eV) 247 (M+, 25), 218 (bp), 175 (28), 147 (33), 70 (65).

EXAMPLE 14

1-(4-Methyl-3-nitro-phenyl)-4-propyl-piperazine

Beginning with 1-(4-methyl-3-nitro-phenyl)-piperazine and 1-bromopropane, the title compound was recovered by the procedure described in Example 2. MS m/z (rel. intensity, 70 eV) 263 (M+, 26), 234 (bp), 191 (19), 70 (84), 56 (40).

EXAMPLE 15

1-Ethyl-4-(4-Methyl-3-nitro-phenyl)-piperazine

Beginning with 1-(4-methyl-3-nitro-phenyl)-piperazine and 1-bromoethane, the title compound was recovered by the procedure described in Example 2. MS m/z (rel. intensity, 70 eV) 249 (M+, 53), 234 (47), 84 (36), 57 (bp), 56 (46).

EXAMPLE 16

1-Allyl-4-(4-Methyl-3-nitro-phenyl)-piperazine

Beginning with 1-(4-methyl-3-nitro-phenyl)-piperazine and allylbromide, the title compound was recovered by the procedure described in Example 2. MS m/z (rel. intensity, 70 eV) 261 (M+, 60), 96 (70), 69 (bp), 68 (48), 56 (73).

EXAMPLE 17

1-Isopropyl-4-(4-Methyl-3-nitro-phenyl)-piperazine

Beginning with 1-(4-methyl-3-nitro-phenyl)-piperazine and 1-isopropylbromide, the title compound was recovered by the procedure described in Example 2. MS m/z (rel. intensity, 70 eV) 263 (M+, 31), 249 (15), 248 (bp), 84 (15), 56 (42).

EXAMPLE 18

1-Butyl-4-(4-Methyl-3-nitro-phenyl)-piperazine

Beginning with 1-(4-methyl-3-nitro-phenyl)-piperazine and 1-butylbromide, the title compound was recovered by the procedure described in Example 2. MS m/z (rel. intensity, 70 eV) 277 (M+, 23), 234 (bp), 191 (17), 70 (64), 56 (33).

EXAMPLE 19

1-(4-Chloro-3-nitro-phenyl)-4-propyl-piperazine

Beginning with 1-(4-Chloro-3-nitro-phenyl)-piperazine and 1-bromopropane, the title compound was recovered by the procedure described in Example 2. m.p. 249° C. (HCl); MS m/z (rel. intensity, 70 eV) 283 (M+, 27), 254 (87), 165 (bp), 153 (78), 56 (90).

EXAMPLE 20

1-(4-Fluoro-3-trifluoromethyl-phenyl)-4-propyl-piperazine

Beginning with 1-(4-fluoro-3-trifluoromethyl-phenyl)-piperazine and 1-bromopropane, the title compound was recovered by the procedure described in Example 2. m.p. 238° C. (HCl); MS m/z (rel. intensity, 70 eV) 290 (M+, 17), 261 (70), 190 (34), 70 (bp), 56 (44).

EXAMPLE 21

1-(3-Fluoro-5-trifluoromethyl-phenyl)-4-propyl-piperazine

Beginning with 1-(3-fluoro-5-trifluoromethyl-phenyl)-piperazine and 1-bromopropane, the title compound was recovered by the procedure described in Example 2. m.p. 242° C. (HCl); MS m/z (rel. intensity, 70 eV) 290 (M+, 34), 261 (bp), 218 (22), 190 (20), 70 (37).

EXAMPLE 22

1-Ethyl-4-(3-fluoro-5-trifluoromethyl-phenyl)-piperazine

Beginning with 1-(3-fluoro-5-trifluoromethyl-phenyl)-piperazine and 1-iodoethane, the title compound was recovered by the procedure described in Example 2; MS m/z (rel. intensity, 70 eV) 276 (M+, 46), 261 (41), 190 (30), 84 (30), 57 (bp).

EXAMPLE 23

1-Butyl-4-(3-fluoro-5-trifluoromethyl-phenyl)-piperazine

Beginning with 1-(3-fluoro-5-trifluoromethyl-phenyl)-piperazine and 1-bromobutane, the title compound was recovered by the procedure described in Example 2; MS m/z (rel. intensity, 70 eV) 304 (M+, 22), 261 (bp), 218 (22), 190 (21), 70 (46).

EXAMPLE 24

1-Isopropyl-4-(3-fluoro-5-trifluoromethyl-phenyl)-piperazine

Beginning with 1-(3-fluoro-5-trifluoromethyl-phenyl)-piperazine and isopropylbromide, the title compound was recovered by the procedure described in Example 2; MS m/z (rel. intensity, 70 eV) 290 (M+, 30), 275 (bp), 190 (20), 84 (23), 56 (64).

EXAMPLE 25

1-(3-Methanesulfonyl-4-methoxy-phenyl)-4-propyl-piperazine

Beginning with 1-(3-Methanesulfonyl-4-methoxy-phenyl)-piperazine and n-Pr-I, the title compound was recovered by the procedure described in Example 2;: MS m/z (rel. intensity, 70 eV)) 312 (M+, 38), 284 (17), 283 (bp), 70 (49), 56 (17).

EXAMPLE 26

1-Butyl-4-(3-Methanesulfonyl-4-methoxy-phenyl)-piperazine

Beginning with 1-(3-Methanesulfonyl-4-methoxy-phenyl)-piperazine and n-Bu-Br, the title compound was recovered by the procedure described in Example 2; MS m/z (rel. intensity, 70 eV)) 326 (M+, 32), 284 (16), 283 (bp), 70 (58), 56 (23).

EXAMPLE 27

1-Ethyl-4-(3-Methanesulfonyl-4-methoxy-phenyl)-piperazine

Beginning with 1-(3-Methanesulfonyl-4-methoxy-phenyl)-piperazine and Et-I, the title compound was recovered by the procedure described in Example 2: MS m/z (rel. intensity, 70 eV)) 298 (M+, 81), 283 (45), 84 (36), 57 (bp), 56 (41).

EXAMPLE 28

1-Isopropyl-4-(3-Methanesulfonyl-4-methoxy-phenyl)-piperazine

Beginning with 1-(3-Methanesulfonyl-4-methoxy-phenyl)-piperazine and isopropylbromide, the title compound was recovered by the procedure described in Example 2: MS m/z (rel. intensity, 70 eV)) 312 (M+, 43), 297 (bp), 84 (35), 71 (33), 56 (73).

EXAMPLE 29

1-Allyl-4-(3-Methanesulfonyl-4-methoxy-phenyl)-piperazine

Beginning with 1-(3-Methanesulfonyl-4-methoxy-phenyl)-piperazine and allylbromide, the title compound was recovered by the procedure described in Example 2: MS m/z (rel. intensity, 70 eV)) 310 (M+, 91), 214 (73), 96 (86), 69 (80), 56 (bp).

EXAMPLE 30

2-Methanesulfonyl-4-(4-propyl-piperazin-1-yl)-phenol 1-(3-Methanesulfonyl-4-methoxy-phenyl)-4-propyl-piperazine (30 mg) was dissolved in 48-% HBr (2 ml) and stirred at 120° C. under an Argon-atmosphere for 3 h. The excess of HBr was then evaporated and absolute ethanol added and evaporated. This procedure was repeated several times to yield an residue of 2-Methanesulfonyl-4-(4-propyl-piperazin-1-yl)-phenol×HBr. MS m/z (relative intensity, 70 eV) 298 (M+, 35), 269 (bp), 226 (15), 199 (12), 70 (62).

EXAMPLE 31

4-(4-Butyl-piperazine-1-yl)-2-methanesulfonyl-phenol

Beginning with 1-butyl-4-(3-Methanesulfonyl-4-methoxy-phenyl)-piperazine, the title compound was recovered by the procedure described in Example 30: MS m/z (rel. intensity, 70 eV)) 312 (M+, 29), 270 (15), 269 (bp), 226 (13), 70 (29).

EXAMPLE 32

4-(4-Isopropyl-piperazine-1-yl)-2-methanesulfonyl-phenol

Beginning with 1-isopropyl-4-(3-Methanesulfonyl-4-methoxy-phenyl)-piperazine, the title compound was recovered by the procedure described in Example 30: MS m/z (rel. intensity, 70 eV)) 298 (M+, 39), 284 (18), 283 (bp), 84 (23), 56 (51).

EXAMPLE 33 cis-4-(4-Chloro-3-trifluoromethyl-phenyl)-2,6-dimethyl-1-propyl-piperazine

Beginning with 5-bromo-2-chlorobenzotrifluoride and cis-2,6-dimethyl-1-propyl-piperazine, the title compound was recovered by the procedure described in Preparation 9: m.p. 256° C. (HCl), MS m/z (rel. intensity, 70 eV)) 335 (M+, 5), 305 (55), 112 (bp), 70 (67), 56 (82).

EXAMPLE 34 cis-4-(4-Fluoro-3-trifluoromethyl-phenyl)-2,6-dimethyl-1-propyl-piperazine

Beginning with 5-bromo-2-fluorobenzotrifluoride and cis-2,6-dimethyl-1-propyl-piperazine, the title compound was recovered by the procedure described in Preparation 9: m.p. 221° C. (HCl), MS m/z (rel. intensity, 70 eV)) 318 (M+, 32), 289 (74), 112 (bp), 70 (71), 56 (85).

EXAMPLE 35 cis-4-(3,4-dichloro-phenyl)-2,6-dimethyl-1-propyl-piperazine

Beginning with 4-bromo-1,2-dichlorobenzene and cis-2,6-dimethyl-1-propyl-piperazine, the title compound was recovered by the procedure described in Preparation 9: m.p. 225° C. (HCl), MS m/z (rel. intensity, 70 eV)) 301 (M+, 24), 271 (64), 112 (bp), 70 (47), 56 (53).

EXAMPLE 36

4-(4-Fluoro-3-trifluoromethylphenyl)-1-propyl-1,2,3,6-tetrahydropyridine

Beginning with 4-(4-fluoro-3-trifluoromethyl-phenyl)-1-propyl-piperidine-4-ol, the titled compound was recovered by the procedure described in Preparation 5: MS m/z (rel. intensity, 70 eV)) 287 (M+, 20), 259 (15), 258 (bp), 177 (17), 147 (21).

EXAMPLE 37

4-(3-Fluoro-5-trifluoromethylphenyl)-1-propyl-1,2,3,6-tetrahydropyridine

Beginning with 4-(3-fluoro-5-trifluoromethyl-phenyl)-1-propyl-piperidine-4-ol, the titled compound was recovered by the procedure described in Preparation 5: MS m/z (rel. intensity, 70 eV)) 287 (M+, 27), 259 (14), 258 (bp), 177 (6), 146 (7).

EXAMPLE 38

4-(2-Chloro-5-trifluoromethylphenyl)-1-propyl-1,2,3,6-tetrahydropyridine

Beginning with 4-(2-Chloro-5-trifluoromethylphenyl)-1-propyl-piperidine-4-ol, the titled compound was recovered by the procedure described in Preparation 5. MS m/z (rel. intensity, 70 eV) 303 (M+, 18), 276 (32), 274 (bp), 177 (6), 128 (5).

EXAMPLE 39

4-(1-Propyl-1,2,3,6-tetrahydro-pyridine-4-yl)-2-trifluoromethyl-phenylamine

4-Pyridin-4-yl-2-trifluoromethyl-phenylamine (270 mg) was dissolved in 1-iodo-propane (2 ml) and heated to 100° C. for 2 h. Then the voilatiles were evaporated and the residue redissolved in abs EtOH (20 ml) and $NaBH_4$ (800 mg) was added portions wise at −20° C. The mixture was then allowed to reach r.t. and stirred over night. To the mixture was added 10% $Na_2CO_3$ solution (20 ml). The aqueous layer was extracted with $CH_2Cl_2$ and the combined organic phases were dried ($MgSO_4$), filtered and evaporated to dryness. The crude product was purified by flash chromatography (MeOH: $CH_2Cl_2$ (1:9 (v/v)). Collection of the fractions containing pure product and evaporation of the solvent afforded pure 4-(1-Propyl-1,2,3,6-tetrahydro-pyridine-4-yl)-2-trifluoromethyl-phenylamine (200 mg). MS m/z (rel. intensity, 70 eV)) 284 (M+, 53), 255 (bp), 144 (40), 127 (39), 70 (39). Rf 0.28 (MeOH)

EXAMPLE 40

2,4-Difluoro-N,N-dimethyl-5-(1-propyl-1,2,3,6-tetrahydro-pyridin-4-yl-benzenesulfonamide Beginning with 2,4-difluoro-N,N-dimethyl-5-pyridin-4-yl-benzenesulfonamide, the titled compound was recovered by the procedure described in Example 39: MS m/z (rel. intensity, 7.0 eV)) 344 (M+, 22), 316 (18), 315 (bp), 207 (10), 164 (9). Rf 0.27 (MeOH)

EXAMPLE 41

4-(3-Methanesulfonyl-4-methoxy-phenyl)-1-propyl-1,2,3,6-tetrahydro-pyridine

Beginning with 4-(3-methanesulfonyl-4-methoxy-phenyl)-pyridine, the titled compound was recovered by the procedure described in Example 39: MS m/z (rel. intensity, 70 eV)) 309 (M+, 31), 281 (12), 280 (bp), 128 (20), 115 (30).

EXAMPLE 42

2-Fluoro-5-(1-propyl-1,2,3,6-tetrahydropyridine-4-yl)-benzonitrile

Beginning with 2-Fluoro-5-pyridine-4-yl-benzonitrile, the titled compound was recovered by the procedure described in Example 39: MS m/z (rel. intensity, 70 eV)) 244 (M+, 24), 217 (16), 216 (bp), 158 (11), 134 (10).

EXAMPLE 43

4-(4-Fluoro-3-trifluoromethylphenyl)-1-propyl-piperidine

Beginning with 4-(4-Fluoro-3-trifluoromethylphenyl)-1-propyl-1,2,3,6-tetrahydropyridine, the titled compound was recovered by the procedure described in Preparation 6: m.p. 195-197° C. (HCl), MS m/z (rel. intensity, 70 eV)) 289 (M+, 4), 261 (15), 260 (bp), 177 (7), 70 (13).

EXAMPLE 44

4-(3-Fluoro-5-trifluoromethylphenyl)-1-propyl-piperidine

Beginning with 4-(3-Fluoro-5-trifluoromethylphenyl)-1-propyl-1,2,3,6-tetrahydrtpyridine, the titled compound was recovered by the procedure described in Preparation 6: m.p. 215° C. (HCl) MS m/z (rel. intensity, 70 eV)) 289 (M+, 4), 261 (15), 260 (bp), 177 (6), 70 (11).

EXAMPLE 45

4-(2-Chloro-5-trifluoromethylphenyl)-1-propyl-piperidine

Beginning with 4-(2-Chloro-5-trifluoromethylphenyl)-1-propyl-1,2,3,6-tetrahydropyridine, the titled compound was recovered by the procedure described in Preparation 6: MS m/z (rel. intensity, 70 eV)) 305 (M+, 4), 290 (3), 278 (32), 277 (15), 276 (bp).

EXAMPLE 46

4-(1-Propyl-piperidin-4-yl)-2-trifluoromethyl-phenylamine

Beginning with 4-(1-Propyl-1,2,3,6-tetrahydropyridine-4-yl)-2-trifluoromethyl-phenylamine, the titled compound was recovered by the procedure described in Preparation 6: MS m/z (rel. intensity, 70 eV)) 286 (M+, 2), 257 (17), 98 (10), 96 (8), 70 (bp), Rf=0.28 (MeOH).

EXAMPLE 47

2,4-Difluoro-N,N-dimethyl-5-(1-propyl-piperidin-4-yl-benzenesulfonamide

Beginning with 2,4-difluoro-N,N-dimethyl-5-(1-propyl-1,2,3,6-tetrahydro-pyridin-4-yl-benzene-sulfonamide, the titled compound was recovered by the procedure described in Preparation 6: MS m/z (rel. intensity, 70 eV)) 346 (M+, 2), 318 (19), 317 (bp), 209 (10), 70 (13).

EXAMPLE 48

4-(3-Methanesulfonyl-4-methoxy-phenyl)-1-propyl-piperidine

Beginning with 4-(3-methanesulfonyl-4-methoxy-phenyl)-1-propyl-piperidine, the titled compound was recovered by the procedure described in Preparation 6: MS m/z (rel. intensity, 70 eV) 311 (M+, 6), 283 (17), 282 (bp), 280 (11), 70 (22), Rf=0.3 (MeOH).

EXAMPLE 49

1-(4-Chloro-3-methanesulfonyl-phenyl)-4-propyl-piperazine

Beginning with 1-(4-Chloro-3-methanesulfonyl-phenyl)-piperazine and 1-iodopropane, the titled compound was recovered by the procedure described in Example 2. MS m/z (rel. intensity, 70 eV)) 316 (M+, 25), 289 (41), 287 (bp), 70 (59), 56 (23)

EXAMPLE 50

1-Allyl-4-(3-Chloro-5-trifluoromethyl-phenyl)-piperazine

Beginning with 1-(3-Chloro-5-trifluoromethyl-phenyl)-piperazine and allylbromide, the title compound was recovered by the procedure described in Example 2. MS m/z (rel. intensity, 70 eV)) 305 (M+, 7), 96 (57), 69 (bp), 68 (48), 56 (69).

EXAMPLE 51

2-Fluoro-5-(1-propyl-piperidin-4-yl)-benzonitrile

Beginning with 2-fluoro-5-(1-propyl-tetrahydropyridin-4-yl)-benzonitrile, the title compound was recovered by the procedure described in preparation 6. MS m/z (rel. intensity, 70 eV)) 246 (M+, 6), 217 (bp), 174 (5), 146 (6), 134 (7).

Syntheses of intermediates used in the above Examples are described in the preparations below.

PREPARATION 1

1-(3-Chloro-5-trifluoromethyl-phenyl)-piperazine

Beginning with 3,5-dichlorobenzotrifluoride (500 mg, 2.32 mmol) and piperazine (1 g, 11.6 mmol), 320 mg of the title compound was recovered by the procedure described in Example 1.

PREPARATION 2

1-(4-Chloro-3-trifluoromethyl-phenyl)-piperazine

Beginning with 5-bromo-2-chlorobenzotrifluoride (602 mg) and piperazine (1 g), 480 mg of the title compound was recovered by the procedure described in Example 1.

PREPARATION 3

1-(3,5-Bis-trifluoromethyl-phenyl)-4-piperazine

Beginning with 1-iodo-3,5-bis (trifluoromethyl)-benzene and piperazine, the title compound was recovered by the procedure described in Example 1.

PREPARATION 4

1-Benzyl-4-(4-chloro-3-trifluoromethyl-phenyl)-piperidine-4-ol (Prepared According to Collection Czechoslav. Chem. Commun. 1973, 38, 3879)

A solution of 5-Bromo-2-chlorobenzotrifluoride (5 g, 19.2 mmol) in dry diethyl ether (40 ml) was added dropwise at room temperature to a mixture of Mg (470 mg) in dry diethyl ether (20 ml) under a stream of Argon (g). The reaction gave rise to a solution of Grignard's reagent. A solution of 1-benzyl-4-piperidone (1.3 g, 6.88 mmol) in dry diethyl ether (30 ml) was added dropwise via syringe at room temperature. The combined mixture was stirred for 1 hour, and finally quenched with saturated ammonium chloride solution (40 ml). The mixture was extracted several times with EtOAc and the combined organic phases were dried ($MgSO_4$), filtered and evaporated to dryness. The oily residue was chromathographed on a silica column using EtOAc:toluene (1:1 (v/v)) as eluent affording the title compound (1.6 g, 64%). MS m/z (relative intensity, 70 eV) 369 (M+, 23), 278 (15), 91 (bp), 65 (16), 56 (21).

PREPARATION 5

1-Benzyl-4-(4-chloro-3-trifluoromethyl-phenyl)-1,2,3,6-tetrahydro-pyridine

1-Benzyl-4-(4-chloro-3-trifluoromethyl-phenyl)-piperidine-4-ol (1.5 g) was dissolved trifluoroacetic acid (35 ml) and refluxed for 24 hours and then $CH_2Cl_2$ (200 ml) was added. The phases were separated and then the organic phase was washed with two portions of 10%-$Na_2CO_3$, dried ($MgSO_4$), filtered and evaporated to dryness. Yield 1.5 g. MS m/z (relative intensity, 70 eV) 351 (M+, 27), 172 (9), 92 (11), 91 (bp), 65 (21).

PREPARATION 6

1-Benzyl-4-(4-chloro-3-trifluoromethyl-phenyl)-piperidine

1-Benzyl-4-(4-chloro-3-trifluoromethyl-phenyl)-1,2,3,6-tetrahydro-pyridine (1.45 g) was dissolved in methanol (40 ml). Concentrated hydrochloric acid (0.2 ml) and 50 mg Pd/C, were added. The resulting mixture was hydrogenated under a hydrogen gas pressure (40 psi) for 1 h and then filtered through a pad of celite. The solvent was evaporated in vacuum and the residue was purified by flash chromatography ($SiO_2$, $CH_2Cl_2$:MeOH, 9:1 (v/v)) to give the pure title compound (1.2 g). MS m/z (relative intensity, 70 eV) 353 (M+, 16), 262 (20), 91 (bp), 65 (18), 56 (14).

PREPARATION 7

4-(4-chloro-3-trifluoromethyl-phenyl)-piperidine

A solution of 1-Benzyl-4-(4-chloro-3-trifluoromethyl-phenyl)-piperidine (1.1 g) in 1,2-dichloroethane (50 ml) was cooled to 0° C. Then α-chloroethyl chloroformate (1.5 g) dissolved in 1,2-dichloroethane (30 ml) was added dropwise at 0° C. The reaction mixture was then brought to reflux for 2 days. The volatiles were evaporated in vacuo and the residue triturated with methanol. The mixture was brought to reflux for 4 hours. The solvent was evaporated to afford the title compound as HCl salt (light brown crystals, 1.0 g) MS m/z (relative intensity, 70 eV) 263 (M+, 34), 262 (22), 83 (22), 57 (60), 56 (bp).

PREPARATION 8

1-(3,4-dichloro-phenyl)-piperazine

Beginning with 4-bromo-1,2-dichlorobenzene (200 mg, 0.88 mmol) and piperazine (91 mg, 1.06 mmol), 98 mg of the title compound was recovered by the procedure described in Example 1.

PREPARATION 9

1-(3-Methanesulfonyl-4-methoxy-phenyl)-piperazine

A mixture of 4-bromo-2-methanesulfonyl-1-methoxy-benzene (0.65 g,), piperazine (0.43 g,), sodium tert-butoxide (0.13 g) BINAP (19 mg) and $[Pd_2(dba)_3$ (27 mg) in dioxane (5 ml) was heated under argon at 100° C. for 24 h. After cooling to room temperature, the reaction mixture was taken up in $Et_2O$ (40-50 ml) and washed with brine (15-20 ml). The organic fraction was dried ($MgSO_4$), filtered and evaporated to dryness. The crude material was purified by flash chromatography on silica gel using $CH_2Cl_2$:MeOH (9:1 (v/v)) Yield 0.14 g: MS m/z (rel. intensity, 70 eV)) 270 (M+, 23), 229 (11), 228 (bp), 148 (7), 56 (17).

PREPARATION 10

4-(4-Fluoro-3-trifluoromethyl-phenyl)-1-propyl-piperidine-2-ol.

Beginning with 4-bromo-1-fluoro-2-trifluoromethyl-benzene and 1-propyl-4-piperidone, the titled compound was recovered by the procedure described in Preparation 4.

MS m/z (rel. intensity, 70 eV)) 305 (M+, 5), 276 (bp), 258 (50), 191 (13), 185 (33).

PREPARATION 11

4-(3-Fluoro-5-trifluoromethyl-phenyl)-1-propyl-piperidine-2-ol

Beginning with 1-bromo-3-fluoro-5-trifluoromethyl-benzene and 1-propyl-4-piperidone, the titled compound was recovered by the procedure described in Preparation 4.

MS m/z (rel. intensity, 70 eV)) 305 (M+, 6), 276 (bp), 258 (34), 258 (34), 185 (14).

PREPARATION 12

2,4-Difluoro-N,N-dimethyl-5-pyridin-4-yl-benzenesulfonamide

5-Bromo-2,4-difluoro-N,N-dimethyl-benzenesulfonamide (400 mg) and 4-pyridine-boronic acid (165 mg) was dissolved in toluene (5 ml) and abs EtoH (5 ml). To the mixture was then added Na2CO3 (200 mg) and $Pd(PPh_3)_4$ (79 mg) under an atmosphere of Argon. The resulting mixture was heated to 90° C. for 18 h. Then $CH_2Cl_2$ was added and the organic phase was washed with water and dried ($MgSO_4$), filtered and evaporated to dryness. The residue was then used without any further purification. (MS m/z (rel. intensity, 70 eV) 298 (M+, 77), 256 (36), 191 (bp), 190 (98), 143 (74).

PREPARATION 13

4-Pyridin-4-yl-2-trifluoromethyl-phenylamine

Beginning with 4-bromo-2-trifluoromethyl-phenylamine, the titled compound was recovered by the procedure described in Preparation 12; MS m/z (rel. intensity, 70 eV)) 238 (M+, 52), 218 (44), 191 (27), 75 (41), 51 (bp).

PREPARATION 14

4-(3-methanesulfonyl-4-methoxy-phenyl)-pyridine

Beginning with 4-bromo-2-methanesulfonyl-1-methoxy-benzene, the titled compound was recovered by the procedure described in Preparation 12; MS m/z (rel. intensity, 70 eV)) 263 (M+, bp), 182 (36), 169 (18), 154 (32), 127 (18).

PREPARATION 15

4-(2-Chloro-5-trifluoromethyl-phenyl)-1-propyl-piperidin-4-ol

Beginning with 4-chloro-3-iodobenzotrifluoride and 1-propyl-4-piperidone, the titled compound was recovered by the procedure described in Preparation 4, MS m/z (rel. intensity, 70 eV)) 321 (M+, 8), 294 (38), 292, (bp), 274 (52), 56 (35).

PREPARATION 16

1-(4-Chloro-3-methanesulfonyl-phenyl)-piperazine

Beginning with 5-bromo-2-chloro-methanesulfonyl-benzene and piperazine, the title compound was recovered by the procedure described in Example 1. MS m/z (rel. intensity, 70 eV)) 274 (M+, 20), 234 (40), 232 (bp), 153 (9), 56 (12).

The following tests were uses for evaluation of the compounds according to the invention.

In vivo Test: Behavior

For behavioral testing, the animals were placed in separate motility meter boxes 50×50×50 cm equipped with an array of 16×16 photocells (Digiscan activity monitor, RXYZM (16) TAO, Omnitech Electronics, USA), connected to an Omnitech Digiscan analyzer and a Apple Macintosh computer equipped with a digital interface board (NB DIO-24, National Instruments, USA). Behavioral data from each motility meter box, representing the position (center of gravity) of the animal at each time, were recorded at a sampling frequency of 25 Hz and collected using a custom written LABView™ application. The data from each recording session were analyzed with respect to distance traveled and small-scale movements, e.g. stops in the center of the behavior recording arena, during the recording session. To determine small-scale movements velocity at each time point is calculated as the distance traveled since the preceding sample divided by the time elapsed since the preceding sample. The number of stops is then calculated as the number of times that the velocity changes from a non-zero value to zero. The number of stops in the center of the behavioral recording arena is calculated as the number of stops occurring at a position at least ten centimeters from the edges of the recording arena. For behavioral testing of habituated rats, the animals were placed in the motility meter boxes 30 minutes before the administration of test compound. Each behavioral recording session lasted 60 or 30 minutes, starting immediately after the injection of test compound. Similar behavioral recording procedures was applied for non-habituated rats, habituated rats and drug pretreated rats. Rats pretreated with d-amphetamine are given the dose 1.5 mg/kg s.c. 5 min before the behavioral session in the motility meter.

In vivo Test: Neurochemistry

After the behavioral activity sessions the rats were decapitated and their brains rapidly taken out and put on an ice-cold petri-dish. The limbic forebrain, the striatum, the frontal cortex and the remaining hemispheral parts of each rat were dissected and frozen. Each brain part was subsequently analyzed with respect to its content of monoamines and their metabolites. The monoaminergic indices analyzed were dopamine (DA), 3,4-dihydroxyphenyl-acetic acid (DOPAC), homovanillic acid (HVA), 3-methoxytyramine (3-MT), serotonin (5-HT), 5-hydroxyindole acetic acid (5-HIAA), and noradrenaline (NA). All monoaminergic indices in the dissected tissue were analyzed by means of HPLC with electrochemical detection as described by Svensson K, et al., 1986, Naunyn-Schmiedeberg's Arch Pharmacol 334: 234-245 and references cited therein.

In vivo Test: Pharmacokinetics in the Rat

To determine oral availability (F); and plasma half life (t1/2) of test compounds of this invention experiments performed in the rat were undertaken. On day one rats were implanted with one catheter in the jugular vein and one catheter in the carotid artery under ketamine anesthesia. On day three test compound is injected the either orally or in the jugular vein catheter. Blood samples are collected during 8 hours from the arterial catheter. The blood samples were heparinized and centrifuged. Plasma is collected from the centrifuged samples and frozen. The levels of test compound were subsequently determined in each sample by means of gas chromatography mass spectrometry (Hewlett-Packard 5972MSD). The plasma samples, taken from the rats of the Sprague-Dawley strain, (0.5 ml) were diluted with water (0.5 ml), and 30 pmol (50 μl) of ((−)-S-3-(3-Ethylsulfonylphenyl)-N-n-propyl-piperidine as internal standard was added. The pH was adjusted to 11.0 by the addition of 25 μl saturated $Na_2CO_3$. After mixing, the samples were extracted with 4 ml dichloromethane by shaking for 20 min. The organic layer was, after centrifugation, transferred to a smaller tube and evaporated to dryness under a stream of nitrogen and subsequently redissolved in 40 μl toluene for GC-MS analysis. A standard curve over the range of 1-500 pmol was prepared by adding appropriate amounts of test compound to blank plasma samples. GC was performed on a HP-Ultra 2 capillary column (12 m×0.2 mm ID), and 2 μl was injected in the splitless mode. The GC temperature was held at 90° C. for 1 minute following injection, and was then increased by 30° C./min to the final temperature of 290° C. Each sample was run in duplicate. The lowest detectable concentration of test compound was generally found to be 1 pmol/ml.

What is claimed is:

1. A substituted 4-(phenyl-N-alkyl)-piperidine compound of Formula 1: (I)

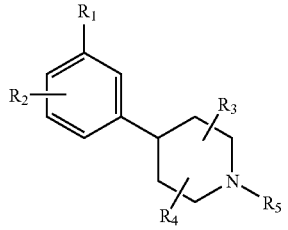

wherein:

$R_1$ is selected from the group consisting of $CF_3$, [$OSO_2CF_3$, $OSO_2CH_3$, $SOR_7$, $SO_2R_7$, $COR_7$,] CN, [$OR_3$, $NO_2$, $CONHR_3$, F, Cl, Br, and I, wherein $R_7$ is as defined below] *and* $SO_2CH_3$;

$R_2$ is selected from the group consisting of F[,] *and* Cl[, Br, I, CN, $CF_3$, $CH_3$, $OCH_3$, OH, and $NH_2$];

$R_3$ is H;

$R_4$ is H; *and*

$R_5$ is [selected from the group consisting of] $C_1$-$C_4$ alkyl[, allyl, $CH_2SCH_3$, $CH_2CH_2OCH_3$, $CH_2CH_2CH_2F$, $CH_2CF_3$, 3,3,3-trifluoropropyl, and 4,4,4-trifluorobutyl;

$R_7$ is selected from the group consisting of $C_1$-$C_3$ alkyls, $CF_3$, $NH_2$ and N(C1-C4 alkyl)2,];

or a pharmaceutically acceptable salt thereof.

[2. A compound or pharmaceutically acceptable salt according to claims 1, wherein $R_2$ is $CH_3$, F or Cl.]

[3. A compound according to claim 1, wherein $R_1$ is $CF_3$, $R_2$ is Cl, $R_3$ is H, $R_4$ is H, and $R_5$ is n-propyl.]

[4. A compound according to claim 1, wherein said compound is 4-(4-chloro-3-trifluoromethyl-phenyl)-1-propyl-piperidine.]

5. A pharmaceutical composition comprising a compound or pharmaceutically acceptable salt [according to] *thereof of* claim 1 and one or more pharmaceutically acceptable carriers, [or] diluents, *or combinations thereof.*

[6. A compound according to claim 1, wherein $R_5$ is selected from the group consisting of n-propyl and ethyl.]

[7. A compound or pharmaceutically acceptable salt according to claim 1, wherein $R_1$ is $SO_2CH_3$, $SO_2CF_3$, $COCH_3$, CN or $CF_3$.]

*8. The compound or pharmaceutically acceptable salt of claim 1, wherein $R_1$ is $CF_3$.*

*9. The compound or pharmaceutically acceptable salt of claim 1, wherein $R_1$ is CN.*

*10. The compound or pharmaceutically acceptable salt of claim 1, wherein $R_1$ is $SO_2CH_3$.*

*11. The compound or pharmaceutically acceptable salt of claim 1, wherein $R_2$ is F.*

*12. The compound or pharmaceutically acceptable salt of claim 1, wherein $R_2$ is Cl.*

*13. The compound or pharmaceutically acceptable salt thereof of claim 1, wherein $R_5$ is selected from the group consisting of butyl, n-propyl and ethyl.*

*14. The compound or pharmaceutically acceptable salt thereof of claim 1, wherein $R_5$ is selected from the group consisting of n-propyl and ethyl.*

*15. The compound or pharmaceutically acceptable salt thereof of claim 1, wherein $R_5$ is butyl.*

*16. The compound or pharmaceutically acceptable salt thereof of claim 1, wherein $R_5$ is n-propyl.*

*17. The compound or pharmaceutically acceptable salt thereof of claim 1, wherein $R_5$ is ethyl.*

* * * * *

UNITED STATES PATENT AND TRADEMARK OFFICE

CERTIFICATE OF CORRECTION

PATENT NO. : RE41,315 E
APPLICATION NO. : 11/904013
DATED : May 4, 2010
INVENTOR(S) : Clas Sonesson et al.

It is certified that error appears in the above-identified patent and that said Letters Patent is hereby corrected as shown below:

Title Page, Item (75) Inventors: should read,

Clas Sonesson, Billdal (SE); Bengt Andersson, deceased, late of Göteborg (SE); by Ingela Marianne Svan, legal representative, Göteborg (SE); Susanna Waters, Göteborg (SE); Nicholas Waters, Göteborg (SE); Joakim Tedroff, Danderyd (SE)

Title Page, Item (73) Assignee: should read,

NSAB, Filial af NeuroSearch Sweden AB, Sverige, Ballerup (DK)

Signed and Sealed this
Twenty-eighth Day of December, 2010

David J. Kappos

David J. Kappos
*Director of the United States Patent and Trademark Office*